US012603015B2

(12) United States Patent
Clarke et al.

(10) Patent No.: US 12,603,015 B2
(45) Date of Patent: *Apr. 14, 2026

(54) ENHANCED CLASSROOM APPLICATIONS, METHODS, AND SYSTEMS USING SENSOR RELAYS INCLUDING SOLAR AND VIRTUAL EMBODIMENTS

(71) Applicant: Lightning Fitness System LLC, New York, NY (US)

(72) Inventors: James Lowell Ramsey Clarke, Washington, DC (US); David Kyle Miller, Fort Washington, MD (US); Chiedo Raymond Ohanyerenwa, Washington, DC (US); John Ramsey Clarke, Lawrence Township, NJ (US); Saul Kinter, Potomac, MD (US)

( * ) Notice: Subject to any disclaimer, the term of this patent is extended or adjusted under 35 U.S.C. 154(b) by 265 days.

This patent is subject to a terminal disclaimer.

(21) Appl. No.: 17/960,155

(22) Filed: Oct. 5, 2022

(65) Prior Publication Data

US 2023/0040917 A1     Feb. 9, 2023

Related U.S. Application Data

(60) Continuation of application No. 15/727,748, filed on Oct. 9, 2017, now Pat. No. 11,645,929, and a (Continued)

(51) Int. Cl.
G09B 19/00     (2006.01)
A61B 5/00     (2006.01)
(Continued)

(52) U.S. Cl.
CPC .............. G09B 5/00 (2013.01); A61B 5/1118 (2013.01); A61B 5/222 (2013.01); A61B 5/4833 (2013.01);
(Continued)

(58) Field of Classification Search
None
See application file for complete search history.

(56) References Cited

U.S. PATENT DOCUMENTS 3,281,964 A * 11/1966 Hewes ..................... B64G 7/00
434/34
5,591,104 A * 1/1997 Andrus ................. A63F 13/428
482/3

(Continued)

OTHER PUBLICATIONS

Report on the filing or determination of an action regarding a patent or trademark dated Apr. 7, 2025 and associated Memorandum opinion at the United States District Court for the District of Delaware in *Lightning Fitness Systems LLC* v. *Precor Incorporated and Peloton Interactive Incorporated* Case 1:24-cv-00012-RGA.

*Primary Examiner* — Sunit Pandya
(74) *Attorney, Agent, or Firm* — Forward Entertainment & Technology, LLC; James Lowell Ramsey Clarke; Chiedo Raymond Ohanyerenwa

(57) ABSTRACT

The present disclosure contains embodiments of an apparatus, system and method designed to facilitate learning or efficient multitasking involving movement and solar energy where users' movement devices process or respond to different stimuli to facilitate users moving while learning, working, or participating in a simulation. In some embodiments this may be accomplished with the aid of a circular treadmill, spherical walkway, or combinable modular trackpads that may be linked to allow a user to lay the apparatus in a path suited for a plurality of environments. The embodiments of the disclosure involve the user moving while processing information and receiving feedback, assistance related to that movement, processing, or any combination thereof while combining the motion of the movement device with the feedback loop sent from sensor relays a user may receive an optimal experience for learning while moving.

(Continued)

112

110

Some embodiments make efficient use of solar energy for classroom education management.

12 Claims, 50 Drawing Sheets

Related U.S. Application Data continuation-in-part of application No. 15/726,370, filed on Oct. 5, 2017, now Pat. No. 12,008,918, said application No. 15/727,748 is a division of application No. 14/217,512, filed on Mar. 18, 2014, now Pat. No. 9,922,574, said application No. 15/727,748 is a continuation-in-part of application No. 14/217,508, filed on Mar. 18, 2014, now Pat. No. 9,818,285, said application No. 15/726,370 is a continuation of application No. 14/217,508, filed on Mar. 18, 2014, now Pat. No. 9,818,285.

(60) Provisional application No. 63/252,604, filed on Oct. 5, 2021, provisional application No. 61/786,840, filed on Mar. 15, 2013.

(51) Int. Cl.

| | |
|---|---|
| *A61B 5/11* | (2006.01) |
| *A61B 5/22* | (2006.01) |
| *B29D 23/00* | (2006.01) |
| *B66B 3/00* | (2006.01) |
| *F16L 11/10* | (2006.01) |
| *F16L 11/12* | (2006.01) |
| *G02F 1/133* | (2006.01) |
| *G08B 21/18* | (2006.01) |
| *G09B 5/00* | (2006.01) |
| *G02F 1/1333* | (2006.01) |
| *G02F 1/1335* | (2006.01) |
| *G02F 1/13357* | (2006.01) |

(52) U.S. Cl.
CPC .............. *A61B 5/486* (2013.01); *B29D 23/00* (2013.01); *B66B 3/002* (2013.01); *F16L 11/10* (2013.01); *F16L 11/12* (2013.01); *G02F 1/133* (2013.01); *G08B 21/18* (2013.01); *G02F 1/13336* (2013.01); *G02F 1/133385* (2013.01); *G02F 1/133526* (2013.01); *G02F 1/133603* (2013.01)

(56) References Cited

U.S. PATENT DOCUMENTS

| | | | | |
|---|---|---|---|---|
| 5,984,839 | A * | 11/1999 | Corkum | A63B 71/0622 |
| | | | | 482/4 |
| 6,458,060 | B1 * | 10/2002 | Watterson | A63B 22/0235 |
| | | | | 482/4 |
| 6,902,513 | B1 * | 6/2005 | McClure | A63B 24/0006 |
| | | | | 482/4 |
| 7,044,891 | B1 * | 5/2006 | Rivera | A63B 21/0053 |
| | | | | 482/8 |
| 8,939,831 | B2 * | 1/2015 | Dugan | A63F 13/45 |
| | | | | 463/31 |
| 8,992,383 | B2 * | 3/2015 | Bilang | A63B 71/0619 |
| | | | | 482/901 |
| 9,358,422 | B2 * | 6/2016 | Brontman | A63B 22/00 |
| 9,367,668 | B2 * | 6/2016 | Flynt | A63B 71/0622 |
| 9,492,709 | B2 * | 11/2016 | Dilli | A63B 24/0087 |
| 9,818,285 | B2 | 11/2017 | Clarke et al. | |
| 2003/0017913 | A1 * | 1/2003 | Stewart | A63B 71/0622 |
| | | | | 482/8 |
| 2006/0205566 | A1 * | 9/2006 | Watterson | H04L 12/40045 |
| | | | | 482/902 |
| 2007/0060451 | A1 * | 3/2007 | Lucas | A61H 7/001 |
| | | | | 482/54 |
| 2009/0124938 | A1 * | 5/2009 | Brunner | A63B 71/0622 |
| | | | | 600/595 |
| 2012/0237911 | A1 * | 9/2012 | Watterson | G10L 15/26 |
| | | | | 482/4 |
| 2013/0288223 | A1 * | 10/2013 | Watterson | G09B 7/00 |
| | | | | 434/428 |
| 2014/0190789 | A1 * | 7/2014 | Clarke | G09B 5/00 |
| | | | | 198/321 |

* cited by examiner

112

110

212

210

218

414                                416

412

834

840

838

826

836

840

812

4900

ENHANCED CLASSROOM APPLICATIONS, METHODS, AND SYSTEMS USING SENSOR RELAYS INCLUDING SOLAR AND VIRTUAL EMBODIMENTS

CROSS-REFERENCE TO RELATED APPLICATIONS

The present application claims priority to U.S. Provisional Patent Application No. 63/252,604, filed Oct. 5, 2021. The entire disclosure of U.S. Provisional Patent Application No. 63/252,604 is incorporated herein by reference. The present application also claims priority as a continuation to U.S. Non-Provisional patent application Ser. No. 15/727,748, filed Oct. 9, 2017. Finally, the present application is a continuation-in-part of U.S. Non-Provisional patent application Ser. No. 15/726,370, filed Oct. 5, 2017.

TECHNICAL FIELD

The general field of the disclosure herein relates to methods or apparatuses involving movement to facilitate learning while moving, efficient multitasking involving movement while the user processes or responds to different stimuli, and the solar energy collection devices to power the involved equipment or the monitoring thereof. The stimuli may include but are not limited to information related to education or entertainment or feedback concerning the user's movement. Monitoring may be conducted on the solar equipment power-draw, efficiency or interoperability. More specifically this movement may be related to coordination, exercise or physiotherapy. The methods and apparatuses of the disclosure involve the user conducting movement, while simultaneously processing information (via: learning; creating through typing, moving, or talking; or being entertained) and receiving feedback or assistance related to that movement, processing, or any combination thereof.

The general field of the disclosure herein also relates to methods, systems, or apparatuses involving rooms with interactive moving walkways, treadmills, or other moving devices. More specifically these moving devices may act in response to the commands of a user or an observer, in unison, or independently. The systems, methods and apparatuses of the disclosure involve a room wherein the user or a plurality of users move on a moving walkway or a plurality of moving walkways, while simultaneously processing (via: learning; creating through typing, moving, or talking; or being entertained) and receiving feedback or assistance related to that movement, processing, or any combination thereof. In some embodiments virtual reality, augmented reality or mixed reality heads may be incorporated to further simulate immersion.

BACKGROUND

Studies related to multitasking have shown that people typically process one task less efficiently when coupled with other tasks (see, e.g., "Cognitive Control in Media Multitaskers" by Ophir and Wagner, Proceedings of the National Academy of Sciences of the United States of America, 2009). Ophir and Wagner found that media related multitasking was distinct from normal multitasking and caused users switching between activities to perform worse than during normal multitasking. Terms such as cognitive distraction, distracted driving, distracted walking, visual distraction, and manual distraction describe the ways in which people lose focus or the ability to provide a timely response to a situation to which they would otherwise be able to respond, due to an additional task.

Conversely, studies have shown that movement can stimulate the functionality of the brain, (see, e.g., "Exercise and the brain: something to chew on" by Van Praag, National Institute of Health, Trends in Neuroscience, 2009). Van Praag finds that optimal maintenance and brain health may depend on exercise and intake of natural products. Furthermore, feedback and assistance while multitasking can be used to stimulate better coordination of movement and any additional tasks. The benefits of movement related to coordination, exercise, and physiotherapy are numerous, including stimulated muscle memory and reflexes due to repetitive movements involving hand-eye coordination, improved health due to weight loss or lowered blood pressure, increased longevity, restoration of function and movement, and the treatment, healing, and prevention of injuries or disabilities. Studies show that increasing numbers of people are living sedentary lifestyles (See e.g. "Amount of Time Spent in Sedentary Behaviors in the United States, 2003-2004" by Charles E. Matthews et. al., American Journal of Epidemiology, 2008). In his study, Matthews found evidence that most Americans, both male and female over the ages of 6-11 now spend over 50% of their time in sedentary behaviors. This is at least partially related to the drawbacks of the information age, in which many people learn, create or conduct business, or are entertained all from a stationary position while observing monitors on their televisions and computers.

While inventions exist that allow movement while creating such as the laptop computer, movement while reading or learning such as tablet processors, or movement while being entertained such as virtual reality headsets like the Vuzix wrap 230 eyewear product, none of these devices are designed specifically for use while moving, and none of them are designed to provide feedback to the user or assistance to the user specifically related to that movement. A method or apparatus specifically designed to allow the user to process information by learning, creating, or being entertained; while moving through coordination, exercise, or physiotherapy; and that aids the user by providing feedback or assistance related to that movement, processing, or any combination thereof; has the potential of being a boon to society.

Studies related to multitasking have also shown that people typically process one task less efficiently when coupled with other tasks (see, e.g., "Cognitive Control in Media Multitaskers" by Ophir and Wagner, Proceedings of the National Academy of Sciences of the United States of America, 2009). Ophir and Wagner found that media related multitasking was distinct from normal multitasking, and caused users switching between activities to perform worse than during normal multitasking. Terms such as cognitive distraction, distracted driving, distracted walking, visual distraction, and manual distraction describe the ways in which people lose focus or the ability to provide a timely response to a situation to which they would otherwise be able to respond, due to an additional task.

Conversely, studies have shown that movement can stimulate the functionality of the brain, (see, e.g., "Exercise and the brain: something to chew on" by Van Praag, National Institute of Health, Trends in Neuroscience, 2009). Van Praag finds that optimal maintenance and brain health may depend on exercise and intake of natural products. Furthermore, feedback and assistance while multitasking can be used to stimulate better coordination of movement and any additional tasks. The benefits of movement related to coordination, exercise, and physiotherapy are numerous, including stimulated muscle memory and reflexes due to repetitive movements involving hand-eye coordination, improved health due to weight loss or lowered blood pressure, increased longevity, restoration of function and movement, and the treatment, healing and prevention of injuries or disabilities. Studies show that increasing numbers of people are living sedentary lifestyles (See e.g. "Amount of Time Spent in Sedentary Behaviors in the United States, 2003-2004" by Charles E. Matthews et. al., American Journal of Epidemiology, 2008). In his study, Matthews found evidence that most Americans, both male and female over the ages of 6-11 now spend over 50% of their time in sedentary behaviors. This is at least partially related to the drawbacks of the information age, in which many people learn, create or conduct business, or are entertained all from a stationary position while observing monitors on their televisions and computers.

While inventions exist that allow movement while creating such as the laptop computer, movement while reading or learning such as tablet processors, or movement while being entertained such as virtual reality headsets like the Vuzix wrap 230 eyewear product, none of these devices are designed specifically for use while moving, and none of them were designed to provide feedback to the user or assistance to the user specifically related to that movement as of the time of the first filing in this patent family. A system method or apparatus specifically designed to allow the user to process, by learning, creating, or being entertained; while moving through coordination, exercise, or physiotherapy; and that aids the user in providing feedback or assistance related to that movement, processing, or any combination thereof; has the potential of being a boon to society.

Furthermore studies have shown that the average human attention span fell from 12 minutes in 1998 to just 5 minutes in 2008 (See e.g. "Stress of Modern Life Cuts Attention Spans to Five Minutes" by Moore, The Telegraph, Nov. 8, 2008) Moore cites a Lloyds TSB Insurance Study which also found that adults over 50 were able to concentrate for younger periods of time than younger people, suggesting that our media heavy and increasingly sedentary lifestyles may be taking its toll on younger generations. If these trends progress they could have potentially devastating effects on the future of our society. Conversely studies have shown that people are capable of longer attention spans when they are doing something they find enjoyable or intrinsically motivating. (See e.g. Dukette, Cornish The Essential 20: Twenty Components of an Excellent Health Care Team. RoseDog Books. 2009) Dukette and Cornish's study shows that attention spans for sustained attention to a freely chosen task range from about 5 minutes in a two-year-old child, to a maximum of 20 minutes in adults.

Classroom designs have remained largely unchanged for over a century. We still have a dozen or more students sitting in classrooms for hours, struggling to pay attention, while a teacher lectures, struggling to keep them engaged—none of this designed around today's society. In rural and minority communities, students often lack access to high-speed broadband further limiting access to high quality teachers. While solutions to bring broadband to these areas may be effective, they won't automatically solve the secondary issue of teacher shortages and would be more cost effective by incorporating solar. Furthermore, they won't solve fix declining attention spans among students. Students could benefit from lessons that adjust to their pace, accessible in a fun way through solar while teachers are informed if they need help. The pandemic highlighted the ability of technology to bring remote learning solutions to classrooms. Some classrooms also adopted standing desks to encourage less distracting behavior and for health benefits. Standing desks alone don't do enough to keep students engaged and create true 21st century high quality education and the benefits over the traditional method of students sitting for 8 hours. Standing alone isn't a substitute for getting exercise, whereas cognitive improvement while walking has been documented.

An invention, that ergonomically incorporates the brains processing of external media with movement and exercise, could be revolutionary in a classroom, simulation, or work setting. An area devoted to such movement could be used as an energy efficient training facility, exercise and learning room, or meditation and rehabilitation area. Utilizing solar energy can bring such solutions to remote areas including outdoor playgrounds while also allowing solar panels to be used as tents to keep students and other users cool and shaded from the sun and the effects of UV radiation.

SUMMARY OF THE INVENTION

Embodiments of the disclosure herein may refer to methods and apparatus including but not limited to users conducting tasks such as learning, working, creating on a computer or other device, or being engaged in a simulation all while moving and outputting sensory information related to those tasks, their movement, or both to one or more devices. Sensory information collected by those devices may include but is not limited to any audio, visual, or tactile information, which may relate to the user's actions or inactions in performing those tasks or in moving. That information may be sent from those devices, herein referred to as sensor relays, to any number of other devices, including but not limited to other sensor relays, one or more computer processors, one or more movement devices. The sensor relay may instead output the information to an output device which converts the information into a form that the user or an observer understands. If the information is received by a computer processor, the computer processor may analyze the information against a set of predetermined set points before sending output information to other devices including but not limited to output devices and movement devices. Movement devices may include any device designed to facilitate the user's movement, including but not limited to treadmills or moving platforms, bicycles, elliptical machines, cable row machines, automatically adjustable weight devices. When receiving a signal from the computer processor, signal relay, or a user or observer who has received feedback regarding the user's sensory information, the movement device may respond accordingly. These designs involve sensors communicating with students and teachers, as well as A/V equipment (including but not limited to LCDs, VR/MR/AR headsets, computer work stations or cellphones), and Exercise equipment (including but not limited to treadmills, circular treadmills, bikes, monkey bars, balance beams, or see-saws) and powered by solar energy. In some embodiments solar panels may be fused with said AV equipment such as a two in one LCD-solar panel where a screen over top of a panel with lights embedded on its face can be used for projection. Other embodiments may involve the interoperability of solar powered headsets and broadband devices. This innovation allows students and teachers to receive information on their performance in different classes, compare it with their baseline, monitor their strengths and weaknesses and see where they need to improve to reach proficiency, in real-time, at their own pace.

One example of an embodiment of this disclosure may be an apparatus containing sensor relays, a treadmill and a headset, all ergonomically designed to transmit signals such that the user receives information while using the treadmill regarding her performance through the headset while simultaneously utilizing the headset to listen to a lecture. Another example may be a treadmill which communicates with a Bluetooth headset so that a microphone in the headset acts as a sensor relay which wirelessly transmits signals to the treadmill indicating when the user is out of breath, thereby causing the treadmill to slow. In some embodiments of the invention, exercise equipment communicates directly with sensors. For instance, a student may be walking on a circular treadmill while a brisk pace while a computer workstation attached to his waist is advanced forward with each step as he types. A sensor on that student's leg may sense perspiration, increased heart rate or a slowed walking pace and send a signal to the treadmill, the computer lesson plan, or both to slow down. Instead, the student may answer too many questions incorrectly and the workstation may send a signal to the device to stop, or speed up with each correct answer, adjusting for performance accordingly. Alternatively, a student may be using a solar powered headset while climbing a jungle gym. The headset may display a countdown for the child to climb to different positions corresponding to math problems. For instance, "what is 72?" is displayed with 4 possible answers corresponding to different areas on the jungle gym. If the child climbs to the one with a "49" hovering over it they will receive feedback indicating their success, perhaps visually on their headset or perhaps from a chime from the WIFI-connected solar outfitted monkey-bars. Stylized animations can also be used to make younger students feel more engaged, and excited about renewable energy challenges, such as fights against Greenhouse Monsters, along with other challenges.

Additionally, the treadmill may include a sensor relay which transmits a signal to the headset wirelessly indicating the user's pace has slowed. A processor may determine that the rate of simulation presented to the user from the headset should be altered. Another example may be a treadmill designed in an adjustable elliptical shape which has sensor relays located along its handle bars to sense the user's position, and relays the users position to an observer's output device, who may then choose to remotely alter the speed of the treadmill. Yet another embodiment may be a user with a visual headset on their face acting as an output device and a sensor relay on their leg. The sensor relay may indicate when the user has exited a perimeter marked by electromagnetic signals sent between other sensor relays located at the boundaries of the perimeter. The sensor relay would then send one or more signals to the user's visual headset interrupting the movie the user was watching on it to tell them they are outside of a designated safe pacing zone.

It is envisioned that this invention may be used to help users engage in movement while effectively processing information related to their tasks. When executed correctly, the users multitasking may be assisted by this system of devices.

The disclosure herein is also related to rooms involving one or more moving devices and may further involve a plurality of users moving while receiving sensory information. Sensory information is defined as audio, visual, and tactile information, which may also be received in the form of feedback to the user, in response to her movements or lack thereof. This room may have several embodiments including but not limited to: a room containing a single treadmill, spanning the length of the room, wherein the user may send a signal to direct the starting or stopping of said treadmill; an area containing a single moving walkway spanning the width of the room, with a raised floor above said moving walkway with holes in the floor so that users entering the holes may access the moving walkway; a room with a plurality of moving devices which the users may utilize while conducting tasks such as learning, working, creating something on a computer device, or being engaged in a simulation all while moving and outputting sensory information related to those tasks, their movement, or both to one or more devices.

Sensory information collected by those devices may include but is not limited to any audio, visual, or tactile information, which may relate to the users actions or inactions in performing those tasks or in moving. That information may be sent from those devices, herein referred to as sensor relays, to one or more other devices, including but not limited to other sensor relays, computer processors or movement devices. The sensor relay may instead output the information to an output device which converts the information into a form that the user or an observer understands. If the information is received by a computer processor, the computer processor may analyze the information against a set of predetermined set points before sending signals to other devices including but not limited to output devices and movement devices. Movement devices may include any device designed to facilitate movement, including but not limited to treadmills or moving platforms, bicycles, elliptical machines, cable row machines, automatically adjustable weight devices. When receiving a signal from the computer processor, signal relay, or a user or observer who has received feedback regarding the user's sensory information, the movement device may respond accordingly.

This disclosure also describes a method for using the room's moving devices to aid in teaching students. This may be accomplished in a variety of ways including but not limited to classrooms with walkways under stationary platforms to allow a teacher to present a lecture to students while the students are in motion on a moving walkway or classrooms where students learn while on various treadmills and the teacher can communicate with them wirelessly. Among the objectives of this disclosure is to provide a room or area which ergonomically incorporates the user's processing and receiving information and feedback while moving. For instance, a room containing an ellipsoidal shaped treadmill interface may allow the user to move in a pattern that allows them to take advantage of centripetal acceleration efficiently, while receiving sensory feedback without the distraction of lagging and falling off of a standard treadmill. The network of treadmills described could be used for conservation of energy for electrical efficiency purposes so that the same energy source powering the network can conserve energy as it powers the sensory interface component. Students and teachers could track their performance in different subjects represented in the shape of a skills chart to make it more fun than the traditional grading method, where rewards like solar pump assisted water blasters are achieved if they reach full proficiency. They could use the aforementioned water blaster in a VR challenge where they have to answer math questions correctly to defeat a raging wildfire, or collaboratively use clean energy solutions to combat enemies like greenhouse monsters.

It is also envisioned that this disclosure will be used for a plurality of users exercising while effectively learning through receiving audio visual information without distractions from multitasking, playing interactive games while moving which may interface with the users movement, listening to or creating audio recordings while exercising effectively, or moving in an immersive technology environment while wearing a translucent headset which displays an image or video on a large monitor visible to all users.

While the preferred embodiments of the invention are shown in the accompanying drawings, it is still to be understood that said embodiments are susceptible to modification and alteration while still maintaining the spirit of my invention.

BRIEF DESCRIPTION OF THE DRAWINGS

Referring to the drawings.

Referring to the drawings.

9 device's walkway can be driven in one or more directions by one or more axle controlled by one or more motors, in this case driving one or more abrasive balls which can control the spin of the movement device's belt.

Figure 29:
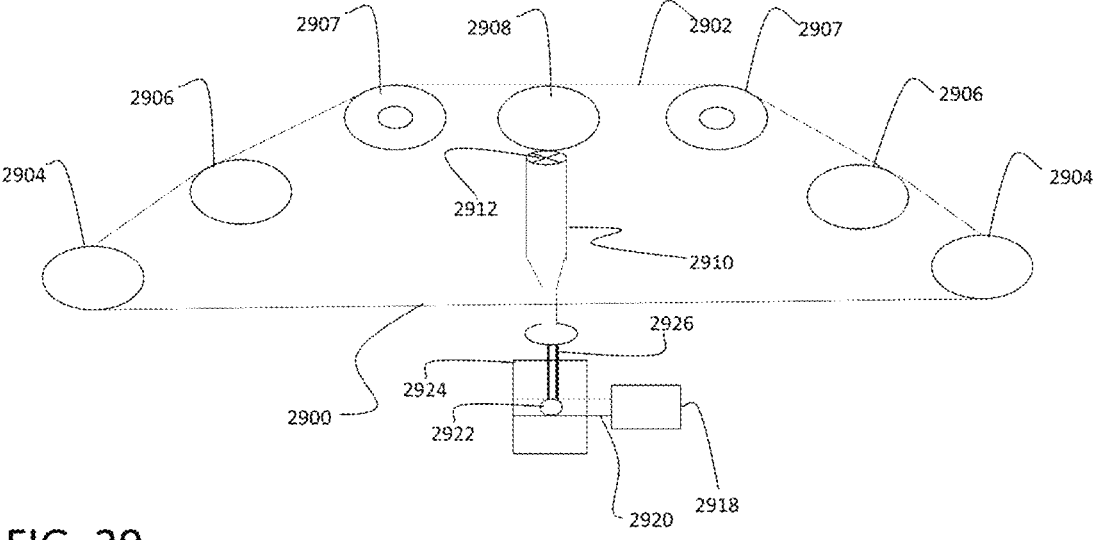

FIG. 29 illustrates a movement device, in this case an omni directional walkway, where direction of the movement device's walkway can be driven by a pivot arm controlled by one or more motors, and in which rollers and balls are located at a plurality of elevations for ergonomic transition angles from the top of the walkway to the lowest traversable point to be achieved.

Figure 30:
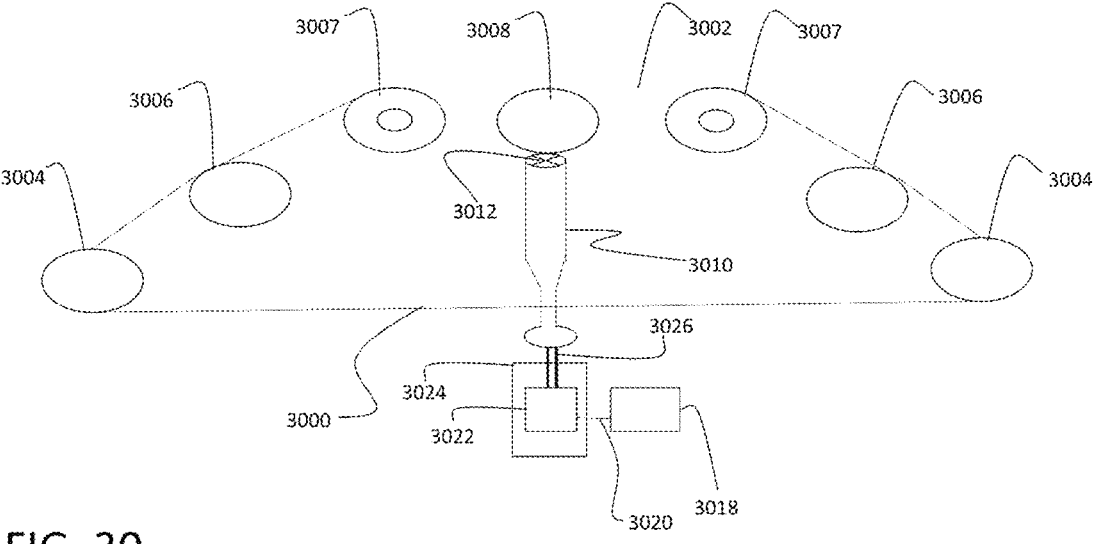

FIG. 30 illustrates a movement device, in this case an omni directional walkway, where direction of the movement device's walkway can be driven in 2 directions by a pivot arm controlled by two motors, and in which rollers and/or balls are located at a plurality of elevations for ergonomic transition angles from the top of the walkway to the lowest traversable point to be achieved.

Figure 31:
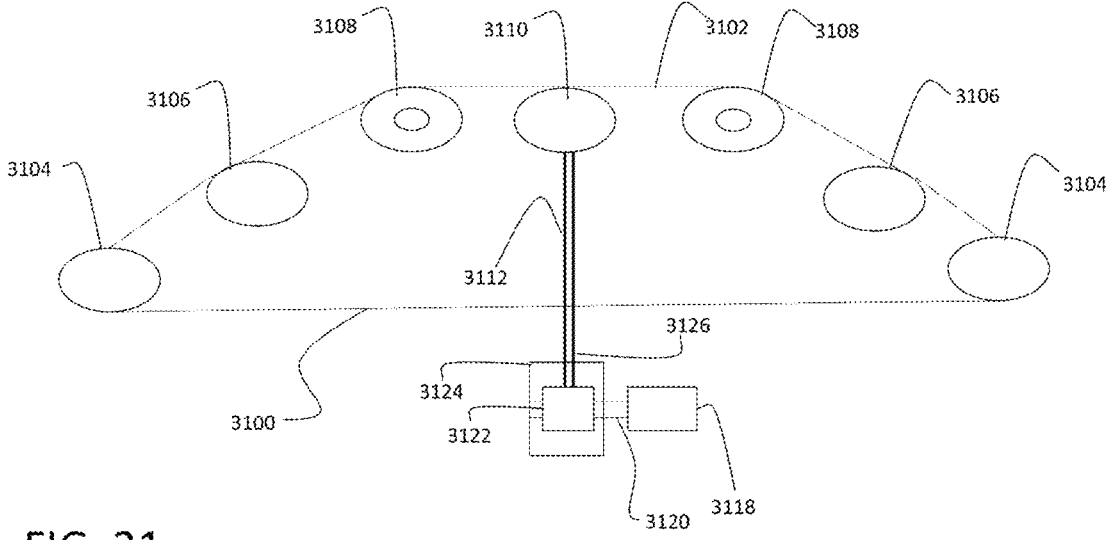

FIG. 31 illustrates a movement device, in this case an omni directional walkway, where direction of the movement device's walkway can be driven in 2 directions by an axle controlled by two motors, in this case driving one or more abrasive balls which can control the spin of the movement device's belt, and in which rollers and/or balls are located at a plurality of elevations for ergonomic transition angles from the top of the walkway to the lowest traversable point to be achieved.

Figure 32:
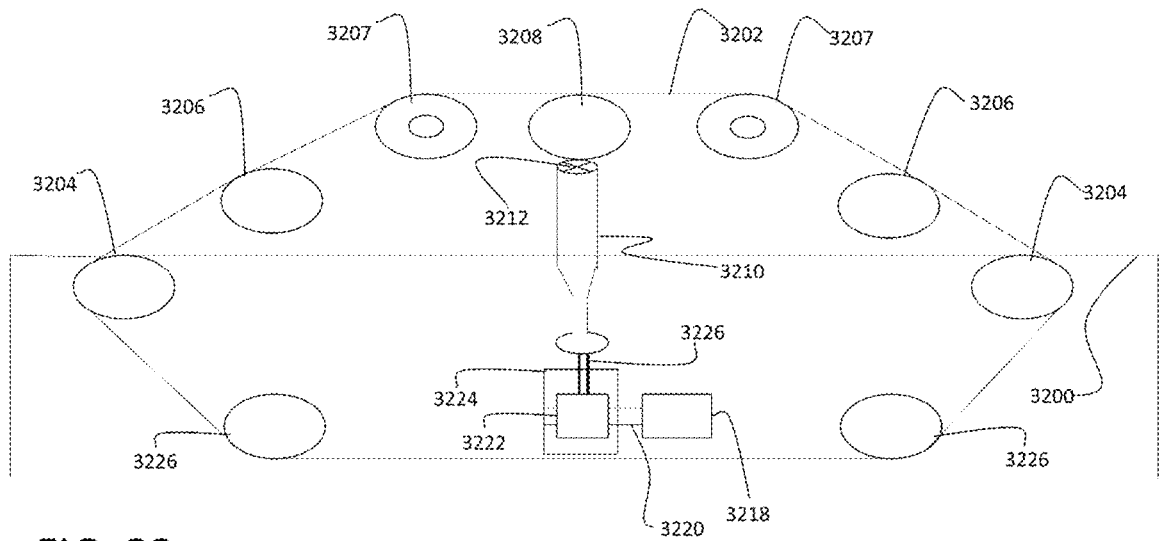

FIG. 32 illustrates a movement device, in this case an omni directional walkway, where direction of the movement device's walkway can be driven in 2 directions by a pivot arm controlled by two motors, and in which rollers and/or balls are located at a plurality of elevations for ergonomic transition angles from the top of the walkway to the lowest traversable point to be achieved, in this case the top of a platform on which sensor relays can be placed to aid in the velocity change.

Figure 33:
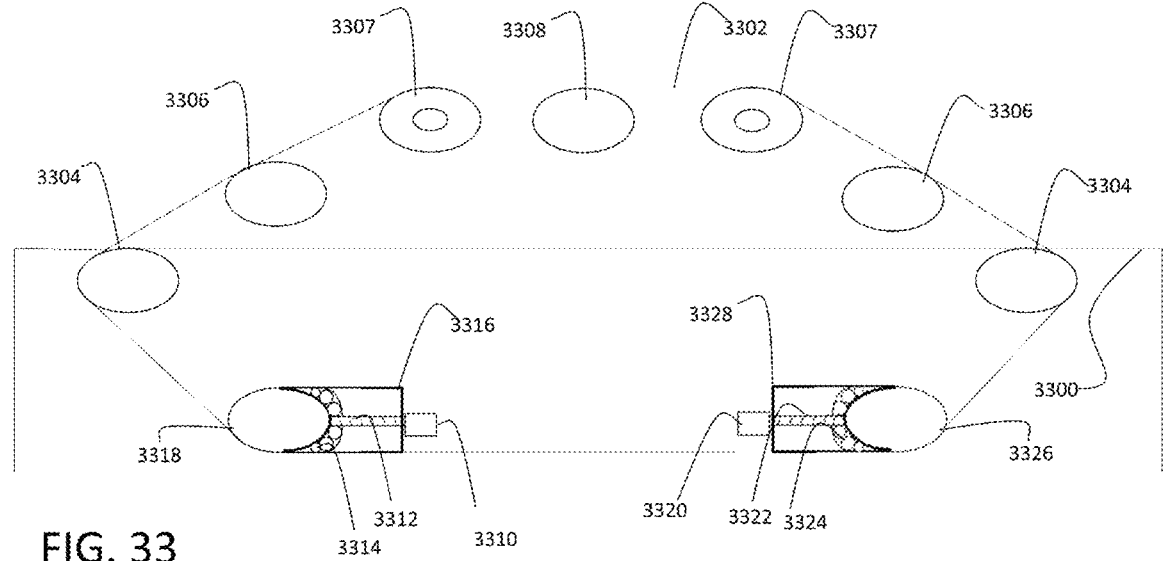

FIG. 33 illustrates a movement device, in this case an omni directional walkway, where direction of the movement device's walkway can be driven in 2 directions by one or more motors in this case driving one or more abrasive balls which can control the movement device's belt velocity, and in which rollers and/or balls are located at a plurality of elevations for ergonomic transition angles from the top of the walkway to the lowest traversable point to be achieved.

Figure 34:
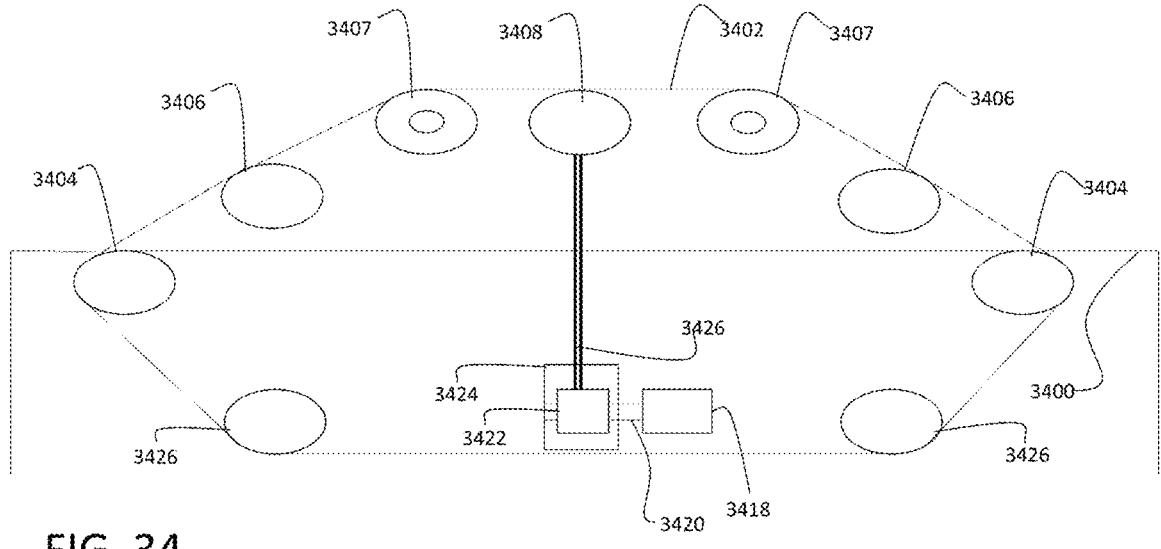

FIG. 34 illustrates a movement device, in this case an omni directional walkway, where direction of the movement device's walkway can be driven in 2 directions by a movable axle controlled by two motors, and in which rollers and/or balls are located at a plurality of elevations for ergonomic transition angles from the top of the walkway to the lowest traversable point to be achieved.

Figure 35:
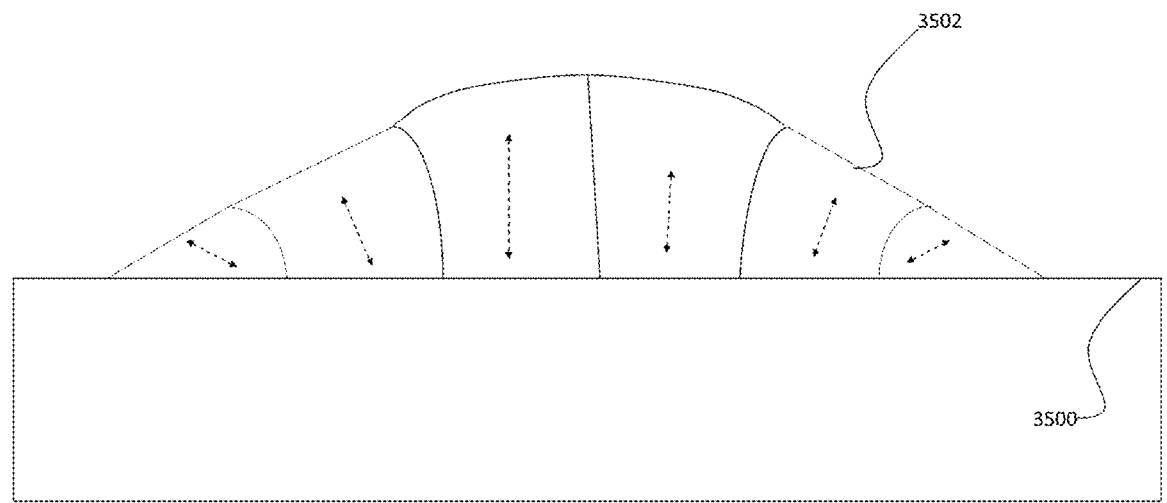

FIG. 35 illustrates a movement device, in this case an omni directional walkway, attached to a resting platform.

Figure 36:
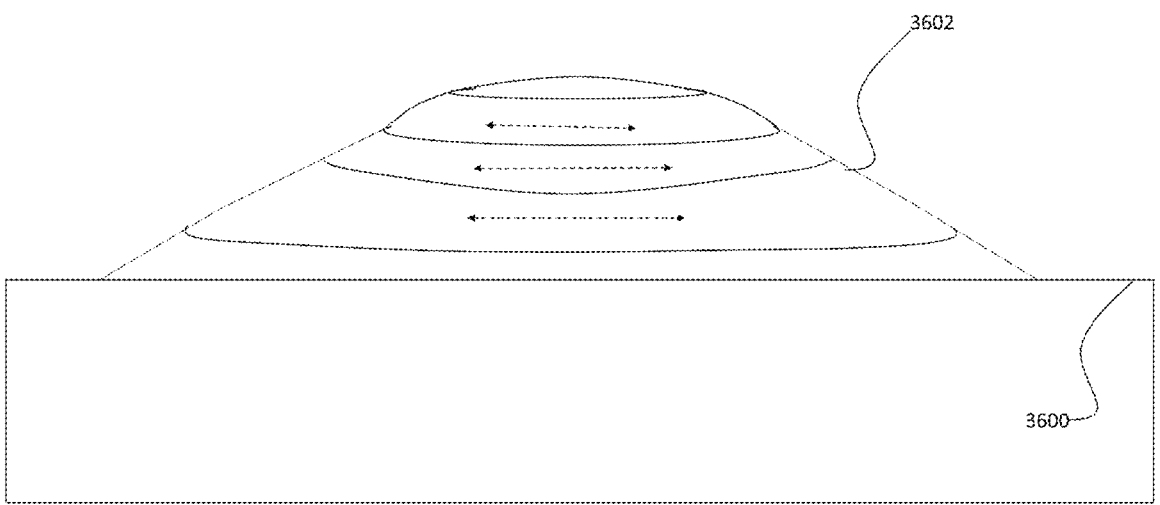

FIG. 36 illustrates a movement device, in this case a spinning walkway, attached to a resting platform.

Figure 37:
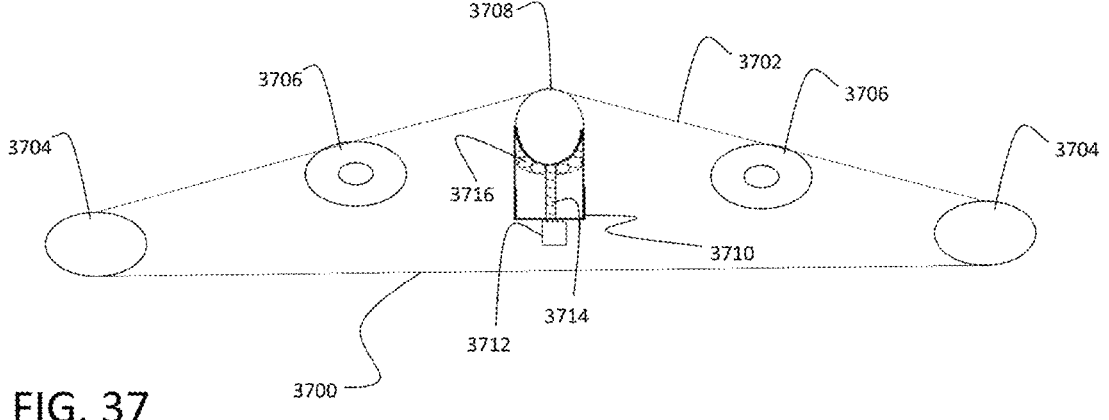

FIG. 37 illustrates a movement device, in this case an omni directional walkway, comprising a motor in this case driving one or more abrasive balls which can control the spin of the movement device's belt, and in which rollers and/or balls are located at a plurality of elevations for ergonomic transition angles from the top of the walkway to the lowest traversable point to be achieved.

Figure 38:
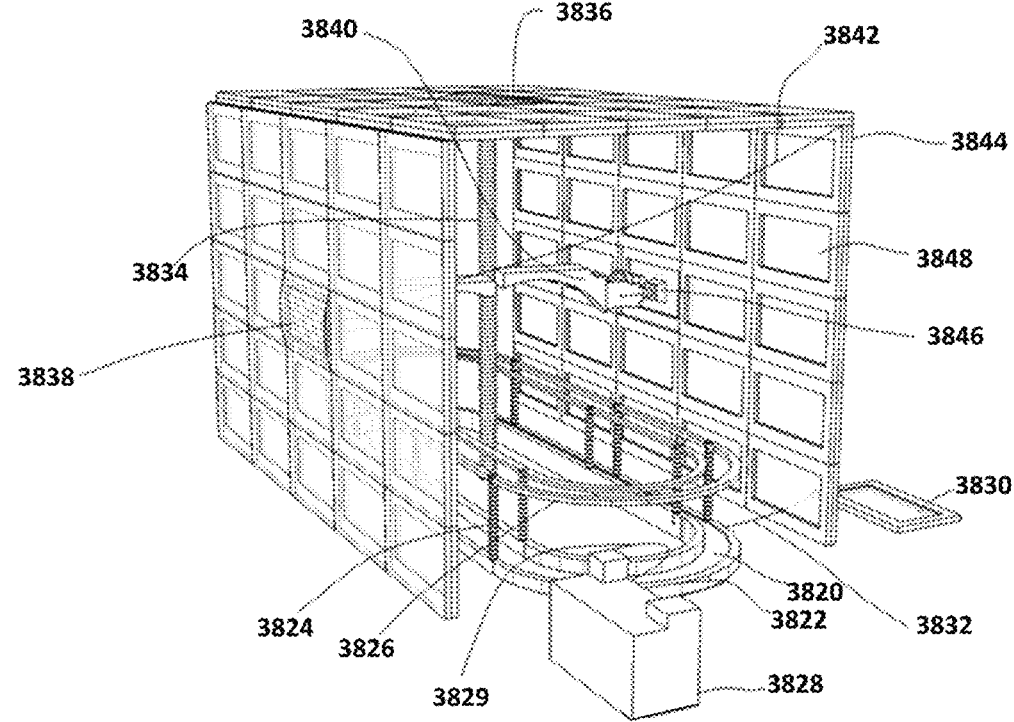

FIG. 38 illustrates a movement device, in this case circular treadmill with a projection tent, solar panel, image array, battery backup power which all interface with the invention in the system of said embodiment.

10

Figure 39:
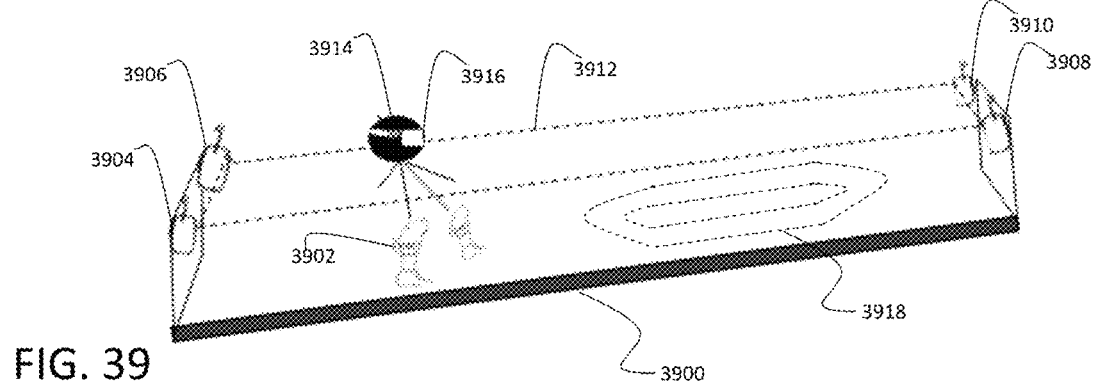

FIG. 39 illustrates a user on an output device wearing an output device and one or more sensor relay's is given and receives feedback from a plurality of sensor relays forming a perimeter of an area. In some embodiments the user's output device may be mixed reality, augmented reality or virtual reality lenses which may show images of walkways and exercise equipment to aid the user.

Figure 40:
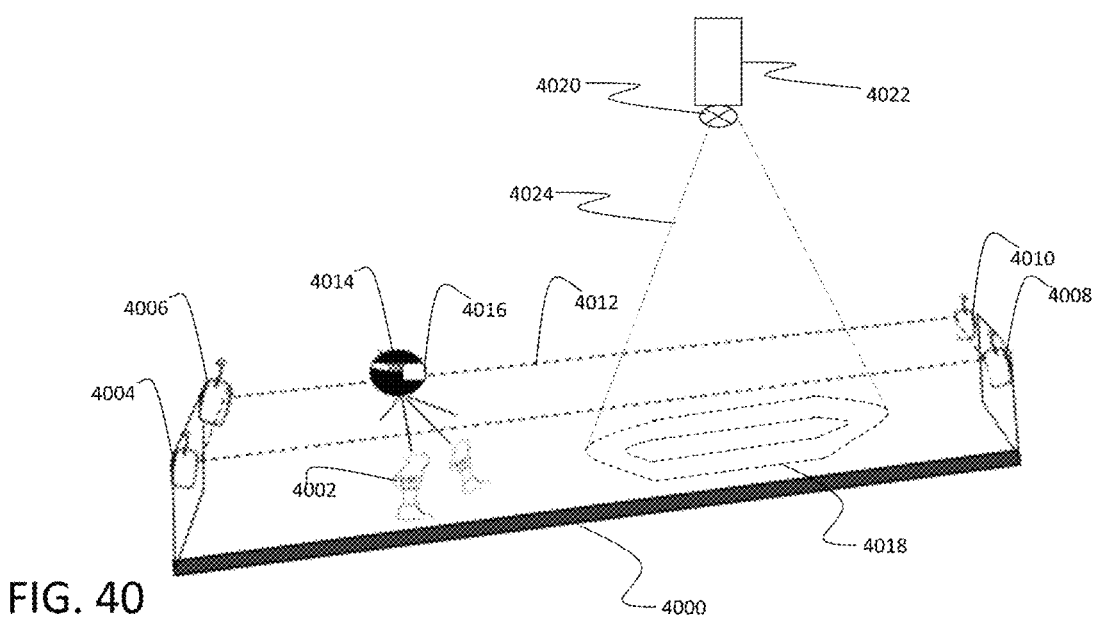

FIG. 40 illustrates a user on an output device wearing an output device and one or more sensor relay's is given and receives feedback from a plurality of sensor relays forming a perimeter of an area. In some embodiments the user's output device may be mixed reality, augmented reality or virtual reality lenses which may show images of walkways and exercise equipment to aid the user and/or the images could be created/augmented by means including but not limited to a projector (as shown) laser display, or holographic image.

Figure 41:
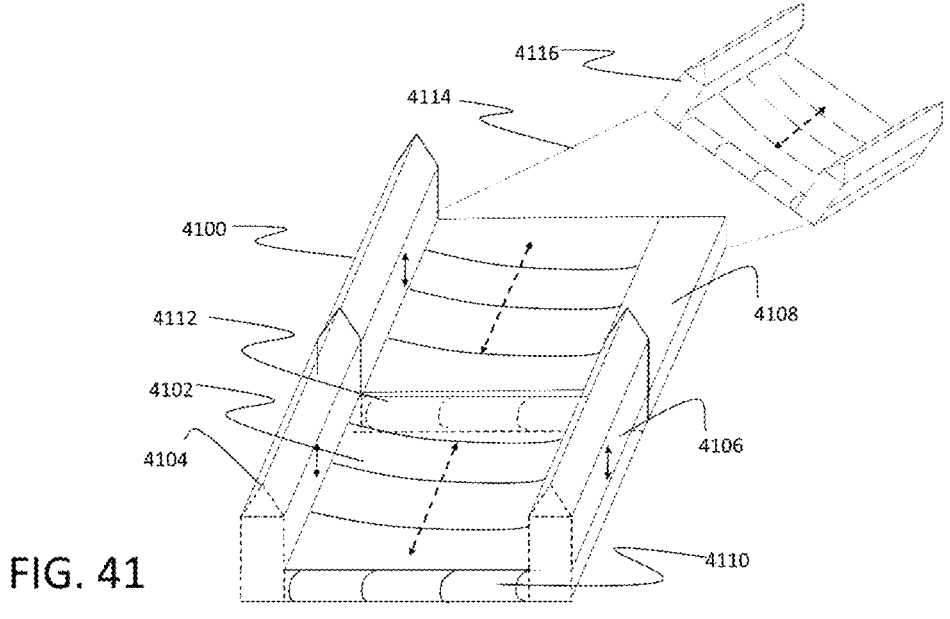

FIG. 41 illustrates a movement device, in this case a modular walkway, such that it's route may be linked together as it is driven by a series of roller. The walkway supports may raise and lower as needed in some embodiments for the user to exit.

Figure 42:
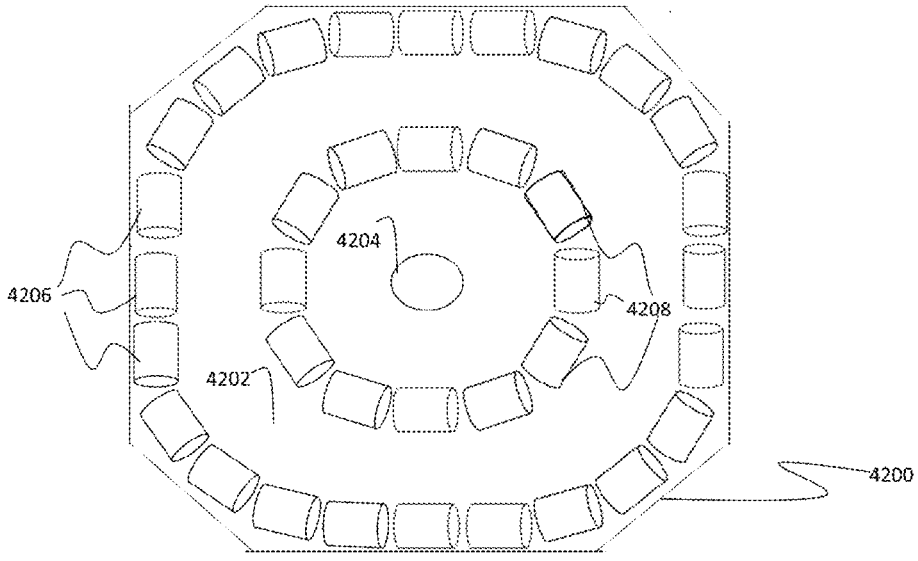

FIG. 42 illustrates an overhead view of a movement device, in this case a multi-directional walkway, where a ball in the middle is used to drive the direction of the belt, as the track glides over the rollers.

Figure 43:
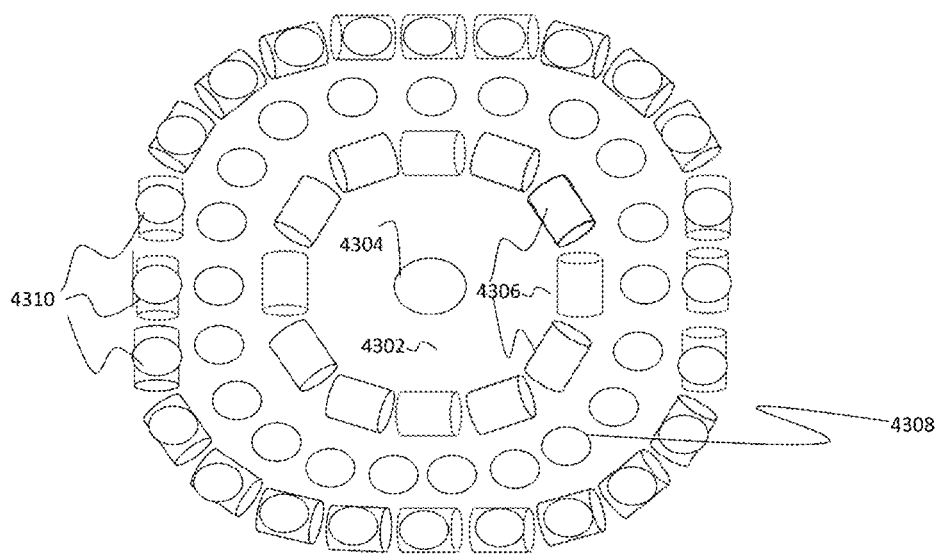

FIG. 43 illustrates an overhead view of a movement device, in this case an omni-directional walkway, where a ball in the middle is used to drive or spin the direction of the belt, as the track glides over the rollers, balls and combinations.

Figure 44:
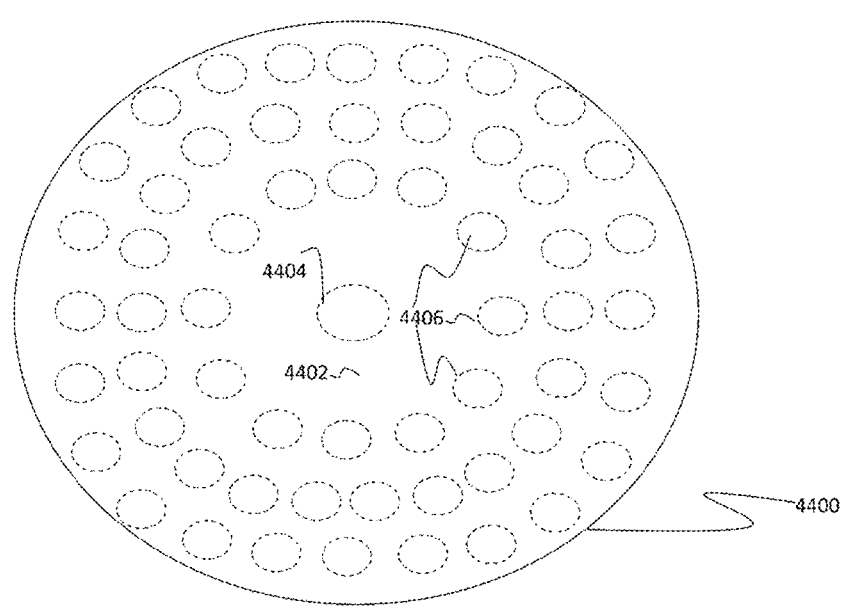

FIG. 44 illustrates an overhead view of a movement device, in this case an omni-directional walkway, where a ball in the middle is used to drive or spin the direction of the belt, as the track glides over a plurality of balls for ease of directional change.

Figure 45:
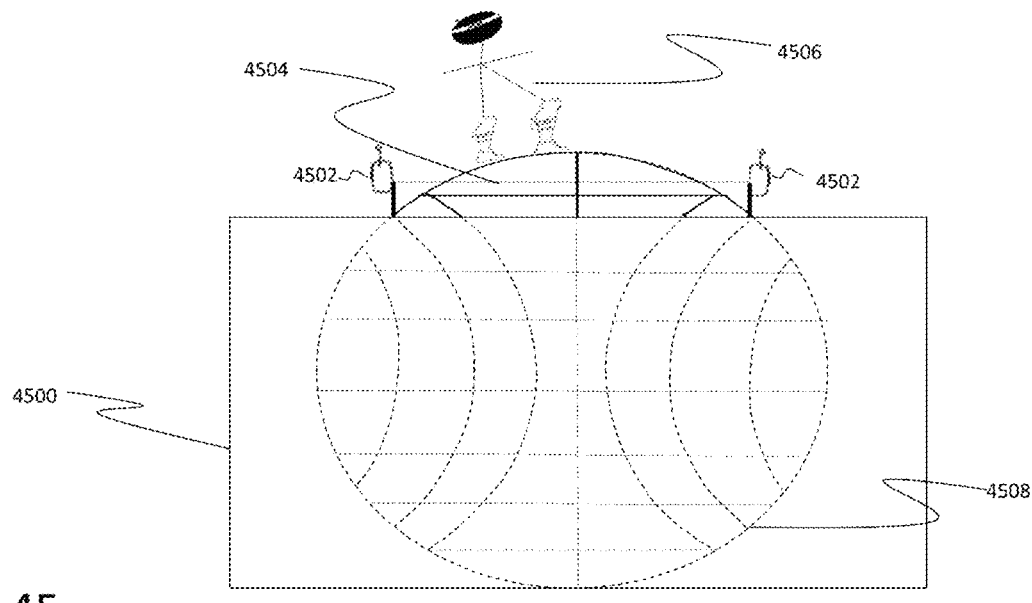

FIG. 45 illustrates a movement device, in this case an omni directional walkway, where the area is bound by sensor relays which communicate with the sensors the user is wearing to determine how to adjust the velocity of the omni-directional walkway to keep the user from walking out or inform them on their output device they are getting close to exiting, or alerting the user in other ways and the walkway traverses is spherically shaped.

Figure 46:
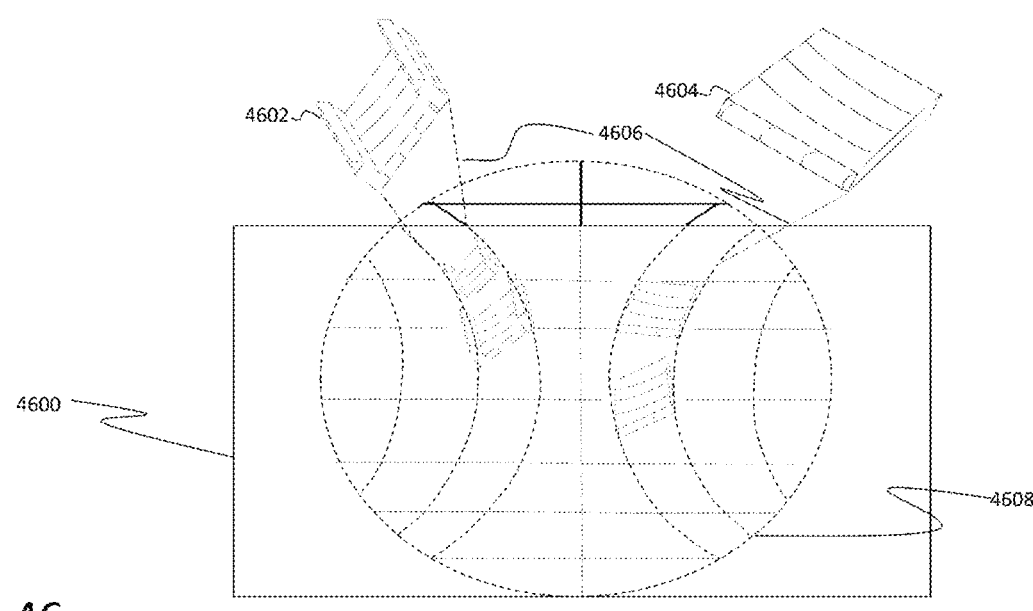

FIG. 46 illustrates a sphere bound to several movement devices, in this case modular walkways, combinable such that their route may be linked together as it is driven by a process including but not limited to the mechanical connections, a series of driven rollers, balls, clips. In some embodiments the modular walkways may have supports that in some such embodiments, may raise and lower as needed in some embodiments for the user to exit.

Figure 47:
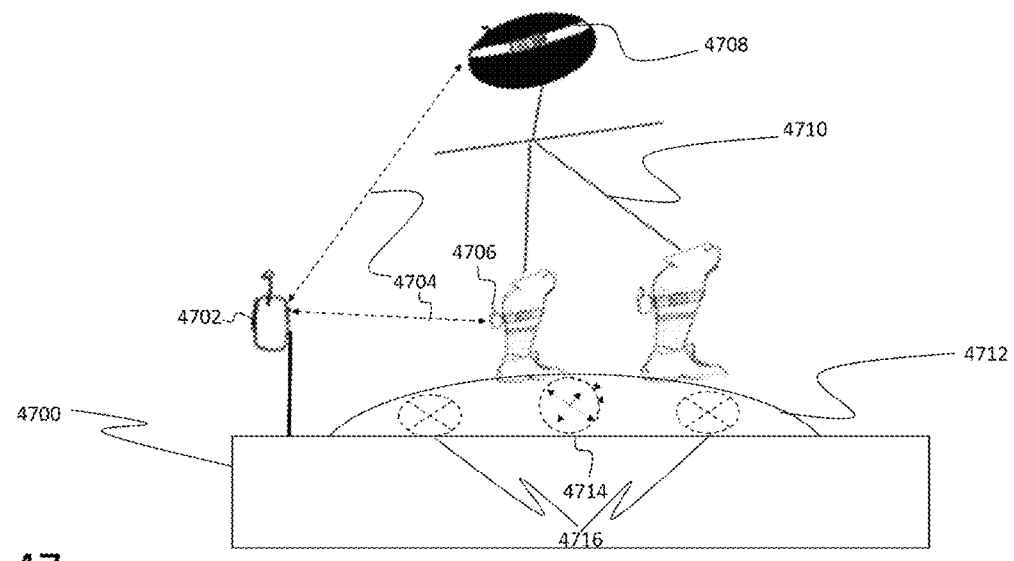

FIG. 47 illustrates a movement device, in this case an omni directional walkway, where the area is bound by sensor relays which communicate with the sensors the user is wearing to determine how to adjust the velocity of the omni-directional walkway to keep the user from walking out or inform them on their output device they are getting close to exiting, or alerting the user in other ways, which further includes sensors for detecting the force of the users weight such that if a user steps off or jumps up from the walkway it can be detected and a signal sent to the movement device or user or an observer's media device other output device.

Figure 48:
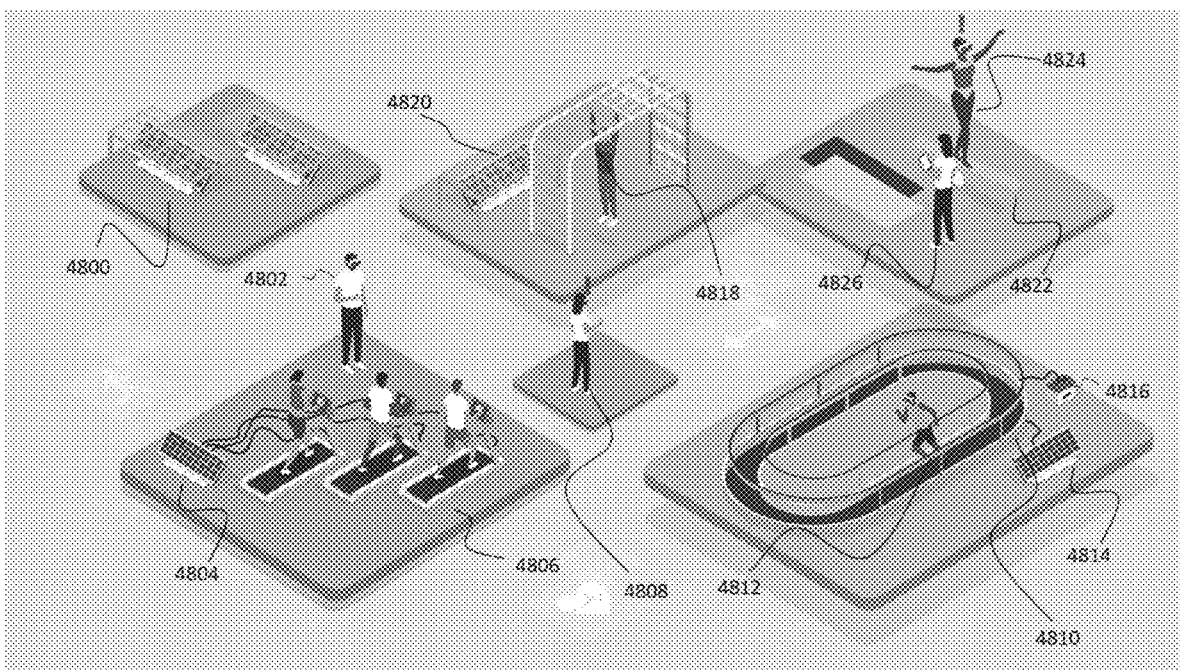

FIG. 48 illustrates a learning classroom powered by solar devices allowing users to move while learning in indoor and outdoor embodiments.

Figure 49:
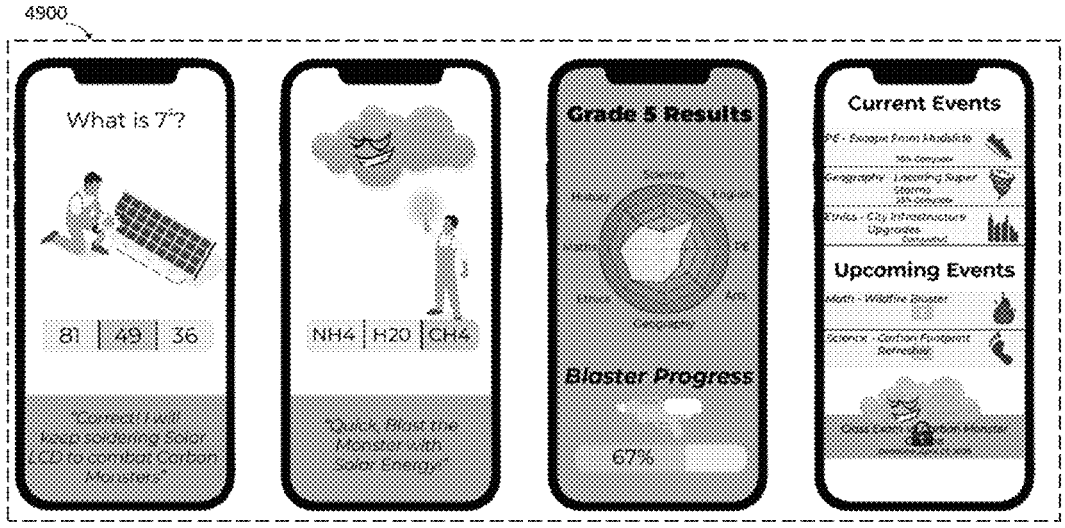

FIG. 49 is an overview drawing of a mobile or virtual application for a learning classroom teaching students the value of solar energy in response to their movements to combine the interactive nature of the classroom with the efficient energy utilized in some embodiments, to help stimulate creativity in facing generational challenges.

Figure 50:
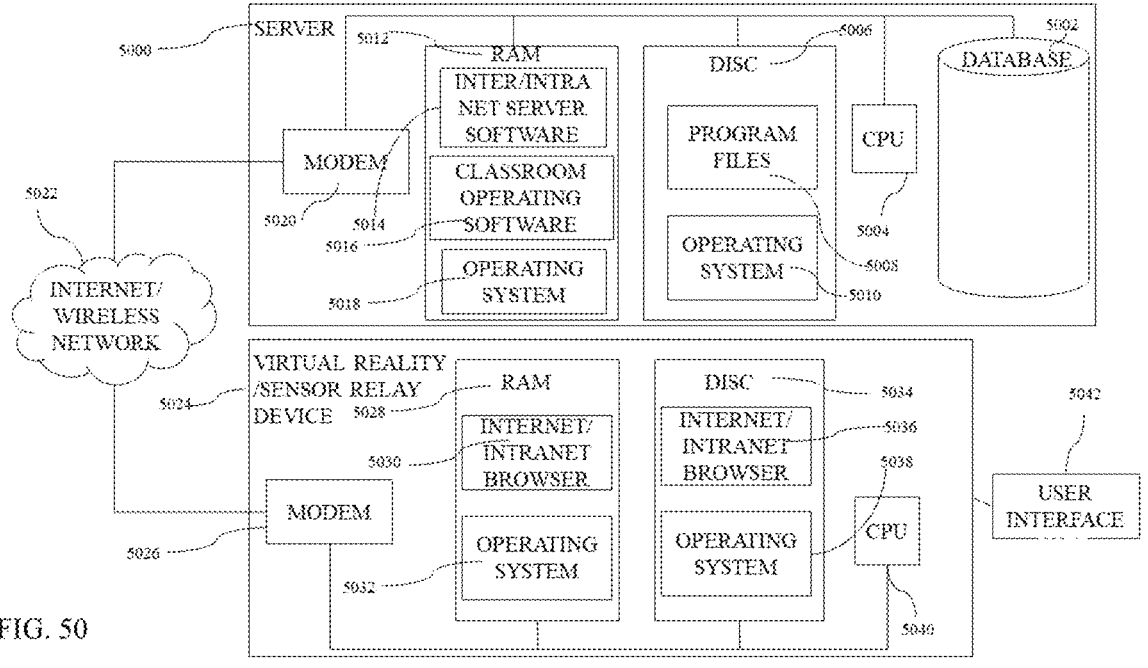

Referring to the drawings, FIG. 50 is an exemplary flowchart showing the typical database hierarchy with data sent to and from a device including but not limited to a virtual reality headset, laptop, or other output device, sensor relays placed on the user, or a mobile device using an application which may process a variety of functions including but not limited to vocal commands, motion tracking, performance on a given task on the operating device, or transmitting communications between students and/or teachers, letting a teacher know how well their students on the network or on a cloud database are performing.

DETAILED DESCRIPTION

In this disclosure the term 'sensor relay' refers to an apparatus composed of any or any combination of devices including but not limited to sensors (including an audio sensor, a visual sensor, a tactile sensor, a gyroscope, an accelerometer, proximity device, or a magnetometer) and relays for sending information such as sensory information or positional information. Sensor relays may include an input or output relays, or any combination therein which may send or receive a signal from the user, an observer, any extension of the user, computer processor or any other sensor relay.

The computer processor is a device which may receive, process, store, or transmit information. The sensor relay may send a signal to the computer processor, another sensor relay, an output device, or a movement device. The computer processor may receive the information from a variety of sources including but not limited to the sensor relays, movement devices, output devices, media devices or any combination thereof. The computer processor may then process the information in a number of different ways including but not limited to analyzing it comparatively against a set point or combination of set points.

Set points are permanent or adjustable values of attributes that may be predefined by individuals, including but not limited to a user, an observer, or a manufacturer. The computer processor may send a signal or combination of signals to a variety of devices including but not limited to other computer processors, sensor relays, output devices, movement device, or media devices.

The output device is a device that may include a computer processor which receives information from a source, including but not limited to a sensor relay or computer processor. The output device may then convert or convey this information, or any combination therein to the user or an observer through any of multiple means, including but not limited to headphones, speakers, a visual monitor or by controlling a movement device. The output device may be or may include a media device.

The media device may have a processor which receives and outputs information as media information. Media information may include learning material (including but not limited to either audio or visual lectures, quizzes, or books) entertainment material (including but not limited to movies, music, or video games), or simulation material (including but not limited to computing material, material directly related to the user's movement for physiotherapy, or exercise assistance material). The media device may adjust its rate of output of media information if directed to do so by its processor. The media device's processor may receive information from a variety of sources including but not limited to users, observers, computer processors, output devices, or sensor relays.

Any signal sent from a sensor relay, computer processor, output device or media device to another can be sent by means including but not limited to wired means (including but not limited to coaxial, vga, hdmi, component, composite, fiber optic, or dvi cables) or wireless means (including but not limited to bluetooth, wifi, or infrared or other electro-magnetic waves). Any signal sent from an output device to either a user, observer, any extension of the user or any sensor relay may be sent via means including but not limited to visual, audio, or tactile means.

In some embodiments where it receives signals, the sensor relay may include audio sensors that can receive input from the user or an observer related to sounds that they make, purposely or otherwise. The audio sensor may be comprised of a variety of audio devices including but not limited to microphones or vibration monitors.

In other embodiments the sensor relay may include visual sensors that can detect movement including but not limited to movement of the user's body, any body parts, extensions of the user's body, or eyes (including but not limited to pupil dilation, eye-crossing, eye wiggles, rapid-eye movement, or normal eye movement). The visual sensor may be comprised of a variety of video devices including but not limited to cameras or optical sensors.

In other embodiments the sensor relay may include tactile sensors which may sense contact (including but not limited to touching, depressing or hitting) or changes in contact (including but not limited to grip modulation, sweating, altered breathing, altered pulse, shaking or swiping) that any part of the user's body, observer's body, or extensions of their bodies (including but not limited to clothes, gloves, or any object directly connected to them) or any combination thereof makes with the sensor or any extension connected to the sensor via wired or wireless means.

In other embodiments the sensor relay may include a gyroscope which may detect changes in the location of one body part or extension of body part in relation to another or from its original position, such as but not limited to those indicating alterations in balance, angular velocity, angular momentum, spin, inertia, or torque. In other embodiments the sensor relay may include an accelerometer which may detect the user's average speed, velocity, or any changes therein. In other embodiments the sensor relay may include a magnetometer which may detect changes in magnetization or proximity of a magnetized object connected to the user or any extension of the user.

In other exemplary embodiments the sensor relays may border the perimeter of a movement device or an area comprising a movement device. In some such exemplary embodiments the movement device may be a trackpad which alternates movement, direction, and/or velocity in response to the user's, movement, direction, velocity, performance on an output device, content on a media device, or biometric data measured against manufacturer defined set points across parameters, observer input or defined set points across parameters, or user input or defined set points across parameters. For example, a movement device may have sensor relays for detecting user weight, or sensor relays around the perimeter that may measure the elevation of user worn sensor relays against the elevation of the movement device. In this example the weight and/or elevation of the user could be parameter(s) with defined/adjustable set points. The set points may be set such that if a user applies a certain weight or jumps to a certain height on the device, the sensor relay measuring said parameters could send a signal to another sensor relay controlling the movement device, output device, or a combination of the two, to illicit a response.

In yet other exemplary embodiments a movement device may be an apparatus herein called an omni-directional treadmill or multi-directional treadmill, that allows the device to move a track-pad linearly back and forth in some such exemplary embodiments, spin the track-pad in other such exemplary embodiments, or move a geometrically shaped walking surface, including but not limited to spherical, elliptical, top-shaped, or dome shape, in a variety of diagonal directions. In some such exemplary embodiments the walking surface of the movement device may move, spin, accelerate, or any combination of the three, directly in response to the user's movements including but not limited to stopping the moment a user breaks the barrier of the perimeter sensor relays, accelerating in the opposite direction and acceleration of a user that is pacing on the device, or moving in response to the content or user response to content on an output device, including but not limited to a user getting a question right or wrong causing the device to accelerate, the device automatically slowing when a tutorial starts, or gradually helping the user descend the platform when a movie ends. Such motion of the movement devices may be accomplished by means including but not limited to pivot arms spinning abrasive balls pushing the trackpad in the opposite direction of the pivot arm, motors driving axles connected to rollers or balls moving the trackpad, a spherical ball spun on one or more axles, which may have one or more trackpads attached to it in some such embodiments or a circular or elliptical treadmill moving back and forth using motors or magnets to propel a trackpad.

In some such embodiments a movement device may be a modular treadmill that can be laid in connectable pieces that allow for contoured or creative placement, and disassembly and reassembly for upgrades or maintenance purposes. In some such embodiments the movement device may come with, be attachable to or have retractable support devices, which may include but are not limited to guide rails, harnesses that move along the track, or barrier walls.

In some embodiments a movement device may be located in a tent of output devices known as display panels. A 'display panel' refers to any panel which may display a feed on a screen, including but not limited to a monitor which displays a single image, a monitor which may display a range of images, a monitor which may display a video, or a monitor which may display a video feed that alters based on the perspective of an observer. The display panel may be further comprised of a variety of tools, including but not limited to a magnifying glass, or have a magnifying glass imbedded directly underneath it; any number of camera's imbedded into or beneath it; or any number of solar panels imbedded into or beneath it. The display panel may display feed it receives from any external or internal feed, including but not limited to cameras, a dvr, or a computer processor.

A movement device may include but is not limited to devices used to facilitate movement or exercise such as a treadmill, bicycle, cable-row, or elliptical machine. In certain embodiments of the disclosure users, observers, sensor relays or computer processors may direct the movement device to alter its settings, including but not limited to its velocity, resistance, incline, or pressure.

Figure 1:
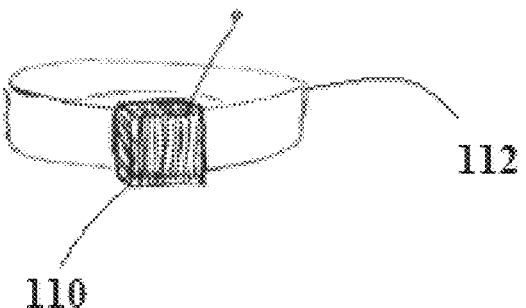
FIG. 1 illustrates an orthogonal view of a portion of an embodiment of the disclosure wherein a relay used for transmitting information regarding the user's movement is transmitted.

As illustrated in FIG. 1 in one embodiment of the disclosure a sensor relay, 110, may be attached to a strap, 112, as signals are sent or received by the sensor relay.

Figure 2:
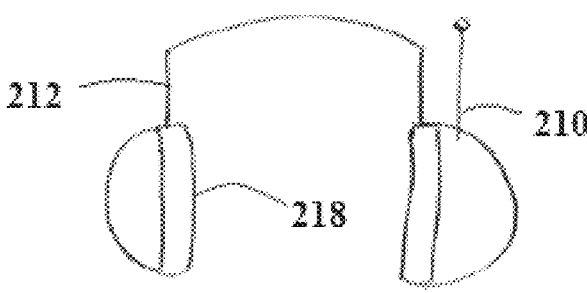
FIG. 2 illustrates a front view of an embodiment of a sensor relay and output device assembly.

As illustrated in FIG. 2 in another embodiment of the disclosure a sensor relay, 210, may be wired, 212, and sends signals to an output device, in this case an audio speaker or headphones with some degree of noise cancelation 218.

Figure 3:
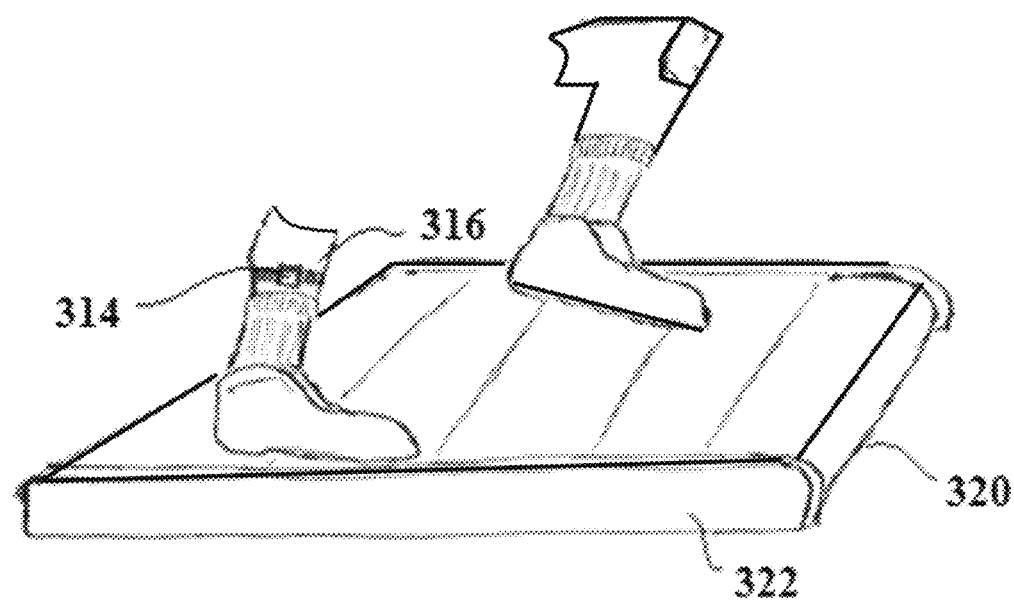
FIG. 3 illustrates an orthogonal view of the relay used for transmitting information regarding the user's movement in position on a human leg in motion on a treadmill or moving walkway.

As illustrated in FIG. 3 in another embodiment of the disclosure a sensor relay, 314, may be fitted to a user's calf, 316. In this embodiment the sensor relay may transmit information about the user's movement, and thereby control a track, 320, on a treadmill, 322, while the user is on said treadmill. However other iterations of the disclosure do not require the user to be on a moving device or the moving device can be non-treadmill moving devices including but not limited to a moving walkway, bicycle, elliptical, track-pad or cable-row.

Figure 4:
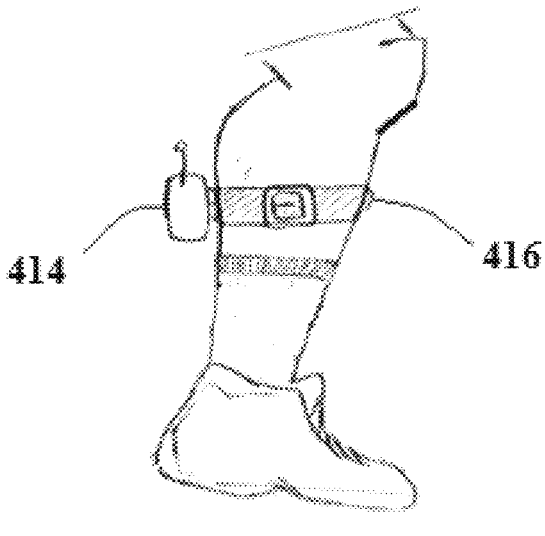
FIG. 4 illustrates an embodiment in which a user's leg movement is detected by a sensor relay.

As illustrated in FIG. 4 in another embodiment of the disclosure a sensor relay, 414, may be fitted to the user's calf, 416, although the user is walking on the ground and the sensor relay sends or receives information concerning the user's proximity to nearby objects to an output device. However other iterations of the disclosure do not require the sensor relay to include a proximity monitor. Sensor relays in this application can be devices including but not limited to accelerometers, audio sensors, tactile sensors, or gyroscopes.

Figure 5:
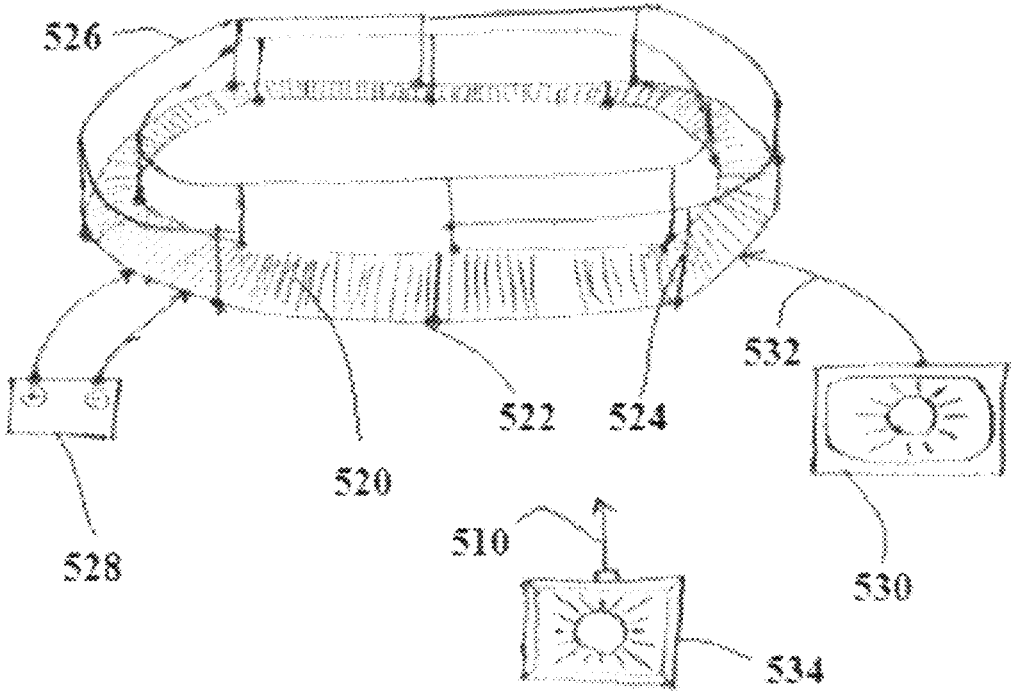
FIG. 5 illustrates an orthogonal view of an embodiment comprising a circular treadmill, one or more solar relays, and battery backup power to supply the treadmill with energy collected from the solar panels or kinetic energy from the user's movement.

As illustrated in FIG. 5 another embodiment of the disclosure may involve a sensor relay, 510, sending signals to a motion device, 520, in the form of a treadmill or moving walkway, 522, which has a circular or elliptical shape. The track the user moves on is in a shape that allows the user to traverse it from beginning to end without fear of going off the track. This has the advantage of allowing the user's speed to significantly differ from the treadmill's speed, without the user having to run into a portion of the treadmill or fall off of the treadmill. Another advantage to this design is that it allows the user more flexibility in movement than a standard treadmill.

In some embodiments the movement of the user may be assisted by: signals sent by the signal relays; a physical guide including but not limited to: supports, 524, which support handle bars, 526; an observer, who receives signals and guides the user; or any combination thereof. In other embodiments the user receives no external assistance in traversing the track, but can effectively traverse in the direction of the track through their own means including but not limited to muscle memory, observation, or mental memory. Additional embodiments of the disclosure may include a dc battery, 528, powering a device, in this case a circular treadmill. In some embodiments the battery may be rechargeable, and in others it may even be synergistically charged by the user's dispensed kinetic energy. In another embodiment the movement device is powered by a solar panel, 530, which can alternatively be used to power the media device, via wires, 532.

In variations of this embodiment, instead of a circular treadmill, the movement device may be any exercise or entertainment equipment including but not limited to a standard treadmill, bicycle, elliptical, a motorized rocking chair, a track-pad which senses the user's location and movements on the pad, or a chair powered by electricity for the purposes of movement or audio output through its embedded speakers or any combination of such devices. The use of rechargeable or portable energy in these embodiments of the disclosure is useful for assisting in maintaining the energy needed to power the device(s) the user is operating, any Signal Relays, computer processors or combinations thereof.

Figure 6:
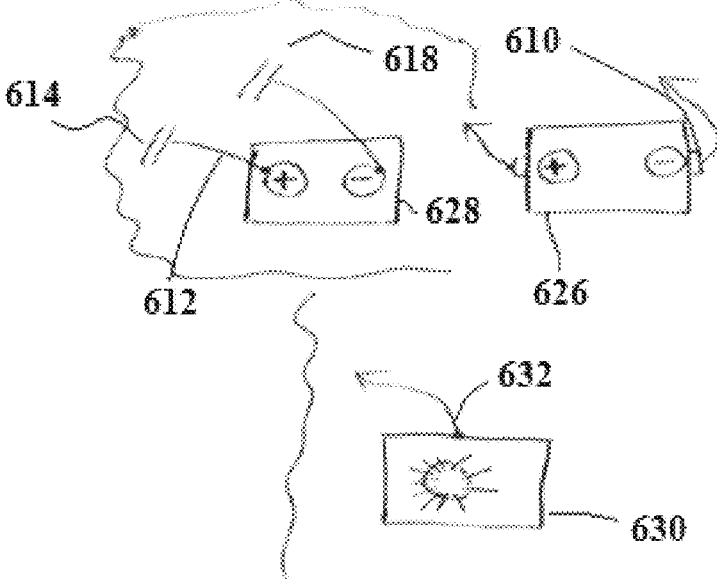
FIG. 6 illustrates an embodiment where a tactile sensory relay is mounted to the user's face.

As illustrated in FIG. 6 in one embodiment of the disclosure the users face may be fitted by an output device, 610, connected, 612, to a sensor relay, 614. The sensor relay can in some embodiments detect tactile information including but not limited to any information on the user's sweat secretions. For instance, the sensor relay's tactile sensor may detect moisture. The sensor relay may then send a signal to a computer processor which analyzes the signal and may send a signal to the movement device to alter the user's velocity, or to the user through an output device making a suggestion to alter the user's velocity. Yet another variation could involve the sensor relay measuring the opening or closing of a sweat gland directly as detected by its tactile sensor designed to measure such movements (on a scale less than a mm$^2$).

Another variation could involve the sensor relay detecting pulse (in one variation being mounted to a vein and designed to detect movement of the vein), and send it to a processor which calculates the beats per minute ("bpm") and uses that bpm to determine the fatigue of the user. In such an embodiment the processor may perform a variety of functions, including but not limited to analyzing the user fatigue computed against a default or a user defined set point, and then sending a signal to either the movement device or to the output device to allow the user to decide whether to slow the device the user is utilizing, cease activity, or neither.

In another variation, the user may be fitted with an array of sensor relays including tactile sensors that may detect the user's: pulse (which may be measured by means including but not limited to measuring vibrations, caused from the beating of the users heart sending blood to the brain, or elsewhere, through the users arteries and veins, any one or more of which the sensor relay is attached to), brain activity (which may be measured by means including but not limited to a tactile sensor relay or sensor relays designed to detect the direct flow of current from the brain to any one or more points on the users scalp), sweat (which may be measured by means including but not limited to a tactile sensor measuring moisture detection or weight over a pre-set threshold or both), or any combination thereof.

The sensor relay may then send the information it detects to a computer processor designed to analyze the information through a variety of means including but not limited to plotting the user's pulse, brain activity, sweat, or any combination therein over time. After analyzing this information against a default or user defined set point, the computer processor may send a signal to the movement device or an output device. A signal to the output device may prompt the decision maker (any user or observer) to alter the movement device's settings, including but not limited to its incline, resistance, pressure, height, velocity, acceleration, or jerk based on those detections, whereas a signal to the movement device would cause said device to automatically adjust its settings.

In other variations the Signal Relay may be attached to the user's nerve cells and detect variations through a variety of means, including but not limited to detecting voltage in a range from −70 mV to 30 mV (+/−15 mV) or instead measure the total displacement out of 100 mV (+/−10 mV), or any combination therein, sending that information to a computer processor which correlates the information against the users learning progress over time. The computer processor can then calculate the learning over time by any number of means, including but not limited to measuring the number of pages the user scrolls per minute, the average speed in which they answer questions over a given period of time, the number of questions which they answer correctly or any variation of responses to learning, entertainment, or other processing activity.

Alternatively the computer processor can send a signal to an output device to provide feedback, allowing the user to control the velocity of the device they are using, their own speed, adjust the device they are using, or adjust their own position, breathing, or any other control factors. Control Factors are any factor related to the user that can be monitored including but not limited to those such as breathing rate or pulse. The computer processor can also control or provide feedback to the output device or media device allowing the user to control the media feed rate based on that information or other nerve activity (including but not limited to detecting current or voltage from automatic nerves, central nerves, or cranial nerves to measure proper functionality according to predefined set points or user defined set points, and determining if the current or voltage from those nerves begins to fall outside of that range, to send a signal to the device for an emergency stop, set off an alarm or send an emergency signal to an observer).

The media feed rate is the rate at which a user is fed material, including but not limited to educational materials such as readings or lectures, entertainment materials such as television or videogames, or user controlled materials which can be downloaded or installed into the media device's processor through a number of means, including but not limited to USB, CD, internet or any combination therein. This can be either controlled by the user's actions, including but not limited to the user turning the page in a book, scrolling down a personal tablet, or changing the slide on a computer slide show; or processor controlled by the actions of a processor, including but not limited to automatically moving the digital image of an electronic display (such as scrolling or turning the page in an electronic book or website), changing the audio content to a song with a faster or slower pace accordingly, or pausing an entertainment movie until the user reaches their preset comfort level threshold.

In certain embodiments this sensor relay, 614, can also be fitted with an audio relay, 618, designed to send signals to the user for them to process including but not limited to verbal commands, beeps, or music related to their performance. In other embodiments the sensor relay may be directly powered by a variety of sources including but not limited to an external battery, 626. In other embodiments, extensions of the sensor relay may be powered by a variety of sources including but not limited to an external battery, 628. In other embodiments the sensor relay or its external rechargeable battery may be wired to any source of energy, including but not limited to a solar panel, 630, wind turbine, electrical outlet, or any combination thereof, and send energy, 632, back to the system.

Figure 7:
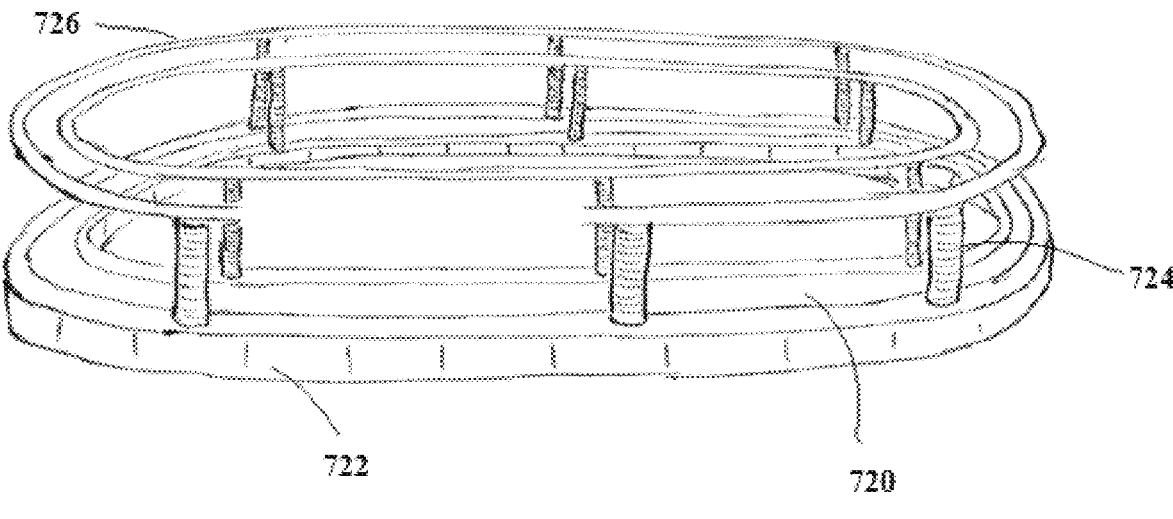
FIG. 7 illustrates a detailed orthogonal view of an embodiment comprising a circular treadmill which may be a component of the disclosure.

As illustrated in FIG. 7 in some embodiments of the disclosure the device may be a track, 720, on top of a circular or an ellipsoidal treadmill, 722, wherein the user would move in a continuous pattern. In certain embodiments this device may include supports, 724, for handle bars, 726, which may be used for a variety of purposes, including but not limited to guiding the user as they traverse the track through the use of their body, hands, or any part of their body and the handle bars.

Figure 8:
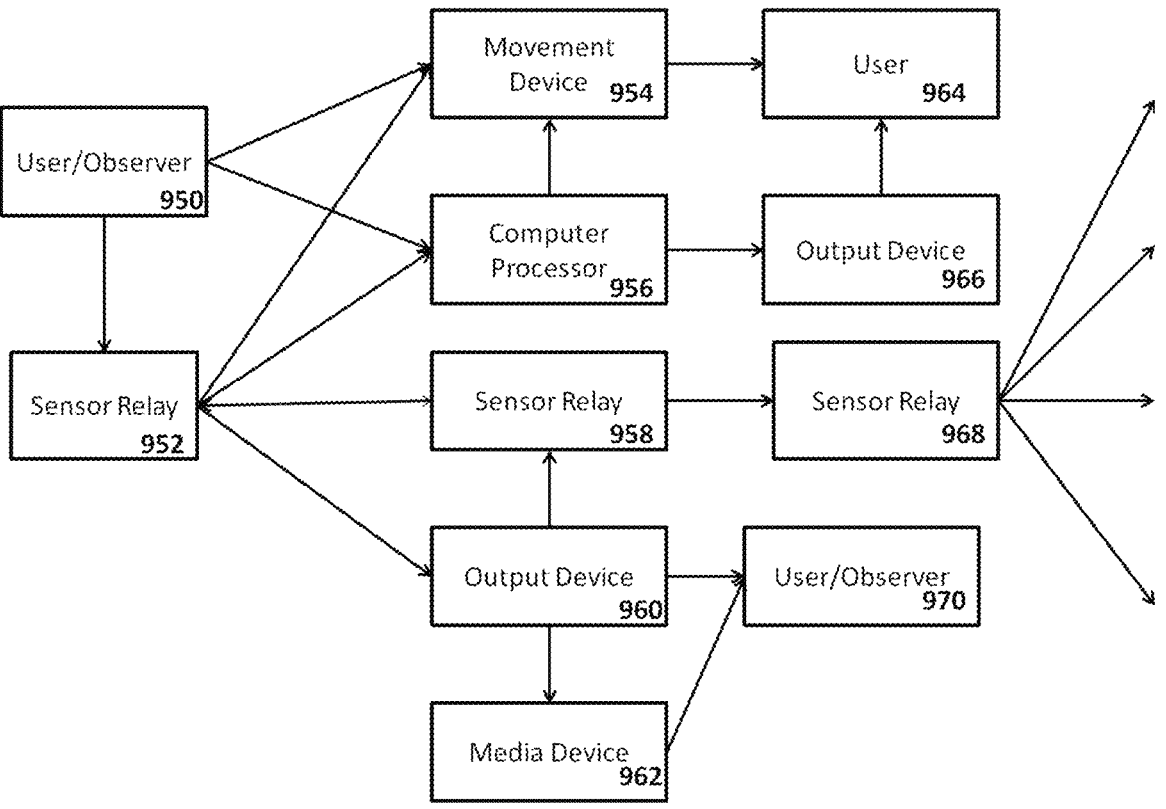
FIG. 8 illustrates a flowchart detailing a method of the disclosure by showing the flow in which users, observers, sensor relays, computer processors, output devices, media devices, and movement devices may act on one another.

As illustrated in FIG. 8 The disclosure itself may involve any number of users or observers, 950, acting on sensor relays, 952, in any number of ways, which may in turn act on any number of movement devices, 954, computer processors, 956, other sensor relays, 958, output devices, 960, or media devices, 962.

Whereas a movement device may only act on any user, 964, the computer processor may act on either the movement device, or an output device, 966. The sensor relay may act on another sensor relay, 968, which may in turn act on any number of movement devices, computer processors, sensor relays, or output devices. The output device may act on a sensor relay, a media device, or a user or observer, 970.

This disclosure also relates to rooms and areas designed to stimulate education, work, meditation, or entertainment while including one or more movement devices. These movement devices may include but are not limited to a treadmill spanning the entire floor of a room, a treadmill spanning the width of the room, a treadmill spanning the length and width of a room with one or more moving platforms above said treadmill, a group of elliptical machines in a classroom setting, a group of treadmills with moving desks imbedded in a work setting. In some embodiments one or more sensor relays may collect information from users and send said information through one or more devices which may translate or analyze said information before sending it to a decision maker or a movement device to aid in the users learning or movement.

Figure 9:
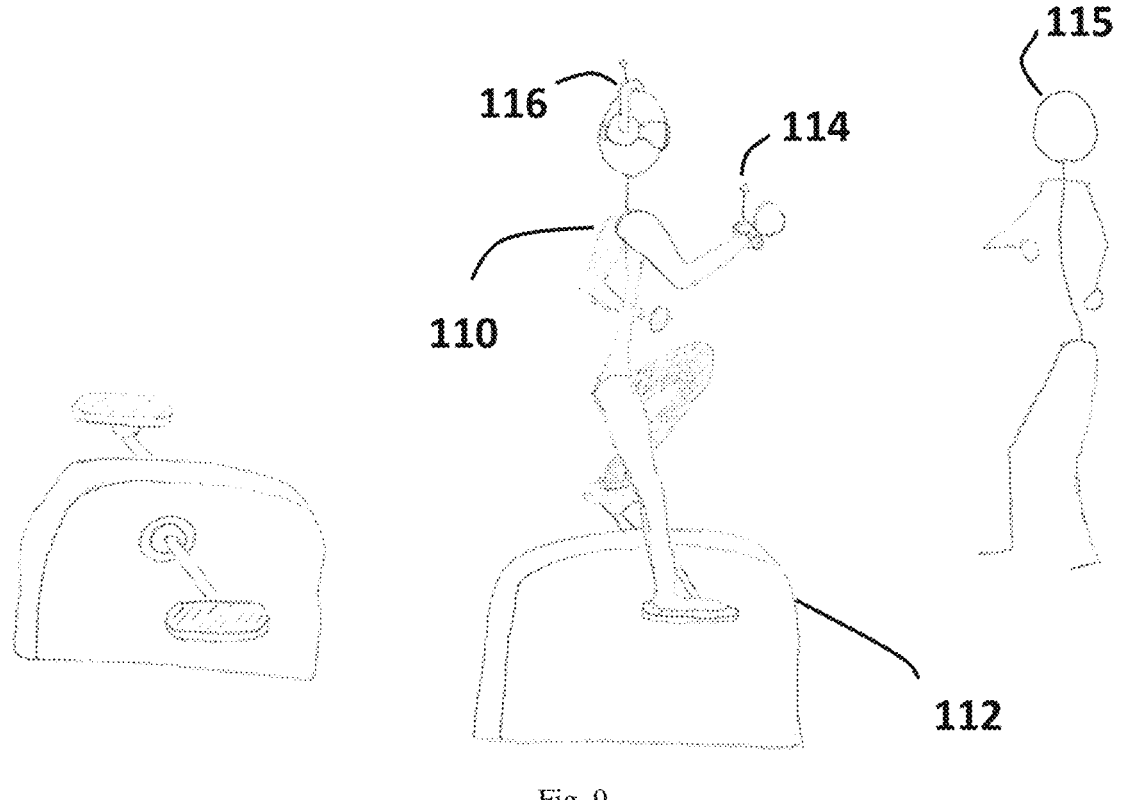
FIG. 9 is an illustration of a room with a plurality of movement devices, wherein a user receives sensory feedback related to his movement and performance through an output device.

As illustrated in FIG. 9 in certain embodiments of the disclosure one or more users, 110, on one or more movement devices, 112, may receive feedback from sensor relays, 114, directed to an output device. An observer, 115, may be present. In some variations this sensor relay may send feedback including but not limited to information concerning the users balance or speed, to an output device, such as a user headset, 116, while the user is reviewing learning content on a pair of virtual glasses, 118. In other variations the sensor relay may send a signal to the movement device or the glasses to pause or slow movement or content respectively.

Figure 10:
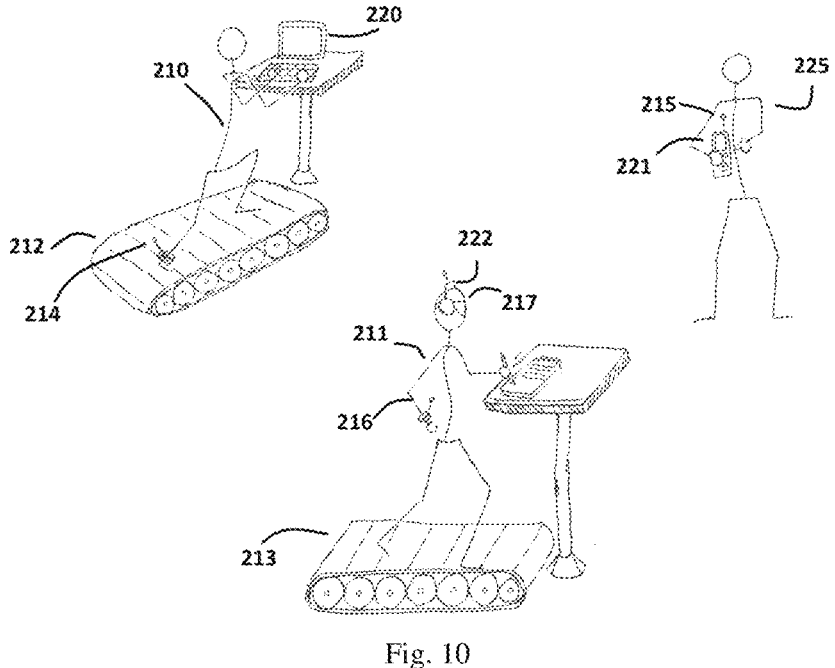
FIG. 10 illustrates a room with a plurality of moving devices and a plurality of users, whose performance related activity is transmitted from sensor relays to an observer's output device.

As illustrated in FIG. 10 in other embodiments of the disclosure a plurality of users, 210, 211, on a plurality of moving devices, 212, 213, may receive feedback from one or more sensor relays, 214, 215, 216 transmitting signals to one or more output devices, 220, 221, 222. In some variations a signal may be sent by one or more sensor relays, monitoring a user working at a standing desk, to an observer, 225, with an output device that receives said signal. That signal may concern an indication that the user is falling asleep as detected by cameras in the user's glasses detecting a slower writing speed than usual. The observer may then make a decision to press a button on their own sensor relay stopping that user's movement. In another variation a signal may be sent by both users' sensor relays on their legs, recording average speed, to the output device of one user, in some instances a computer terminal, on which the user can see that they are lagging behind the other user, and may decide to slow their typing speed and focus on movement, to match or outpace a rival user.

Figure 11:
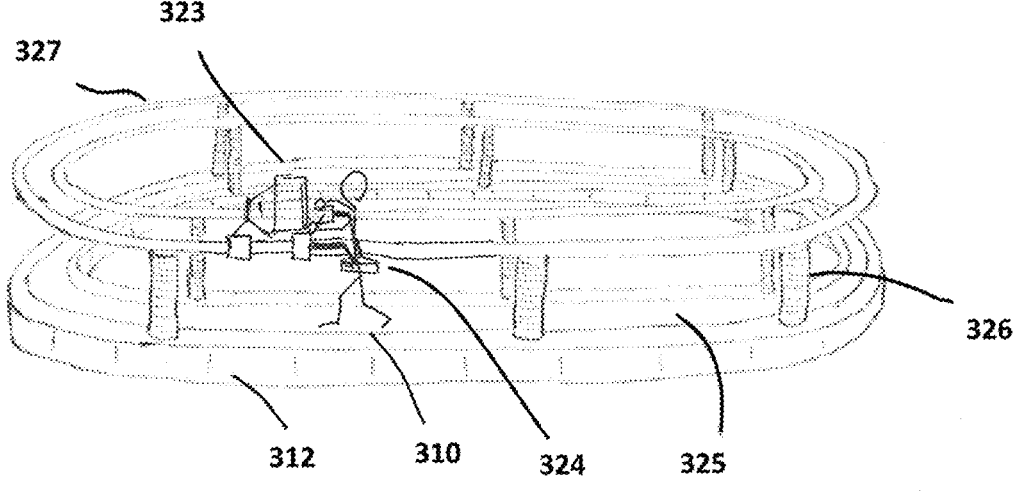
FIG. 11 illustrates a room with a moving device comprising a work station which moves in response to the user's movement.

As illustrated in FIG. 11 in another embodiment of the disclosure a user, 310, utilizing a movement device, 312, (in this case a circular treadmill) may operate a media device, 323, (in this case a computer) which moves in harmony with their own movements. This harmonious movement may be accomplished by a variety of methods, including but not limited to a user with a harness, 324, which is attached to both the user's waist and a set of rods, which cause the desk of the computer to move in response to the user's movements, as the user walks along a track, 325, on top of the circular treadmill. In certain embodiments this device may include supports, 326, for handle bars, 327, which may be used for a variety of purposes, including but not limited to guiding the user as they traverse the track through the use of their body, hands, or straps attached to the user's body, or any part of their body and the handle bars.

Other methods of accomplishing this harmonious movement may involve a media device with a visual sensor relay in the form of cameras, which detects the users hand movement, and sends a signal to a motor, to slide the keyboard desk in and out accordingly, so that the user may type fluidly while still moving slightly.

Figure 12:
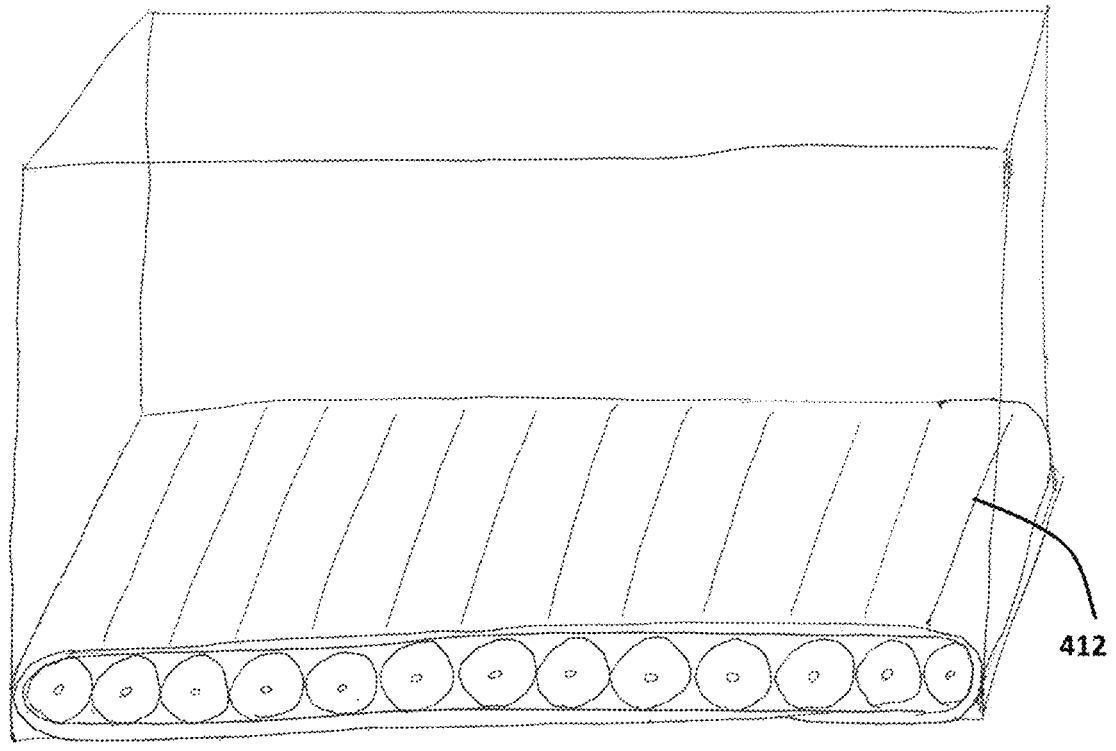
FIG. 12 illustrates a room wherein the entire floor is a moving walkway.

As illustrated in FIG. 12 another embodiment of the disclosure may involve a room wherein a treadmill, 412, spans the entire floor. This may have uses including but not limited to: group training exercises, a classroom where a monitor on the front wall displays a lecture to students moving at a slow walking pace on the treadmill, or a brainstorming room allowing users to walk and engage in comfortable discourse.

Figure 13:
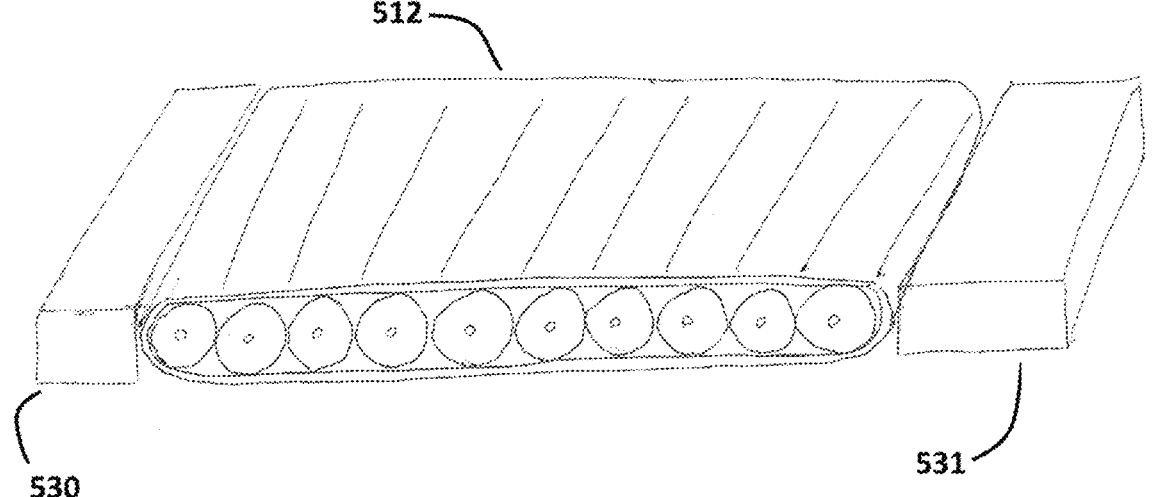
FIG. 13 illustrates a room with a moving walkway spanning the width of the room.

As illustrated in FIG. 13 another embodiment of the disclosure may involve a room wherein a treadmill, 512, spans the entire width of the room. This may allow space for stationary platforms, 530, 531, which may be used in some variations for user rest areas, or an area for an observer to stand while giving the users a seminar.

Figure 14:
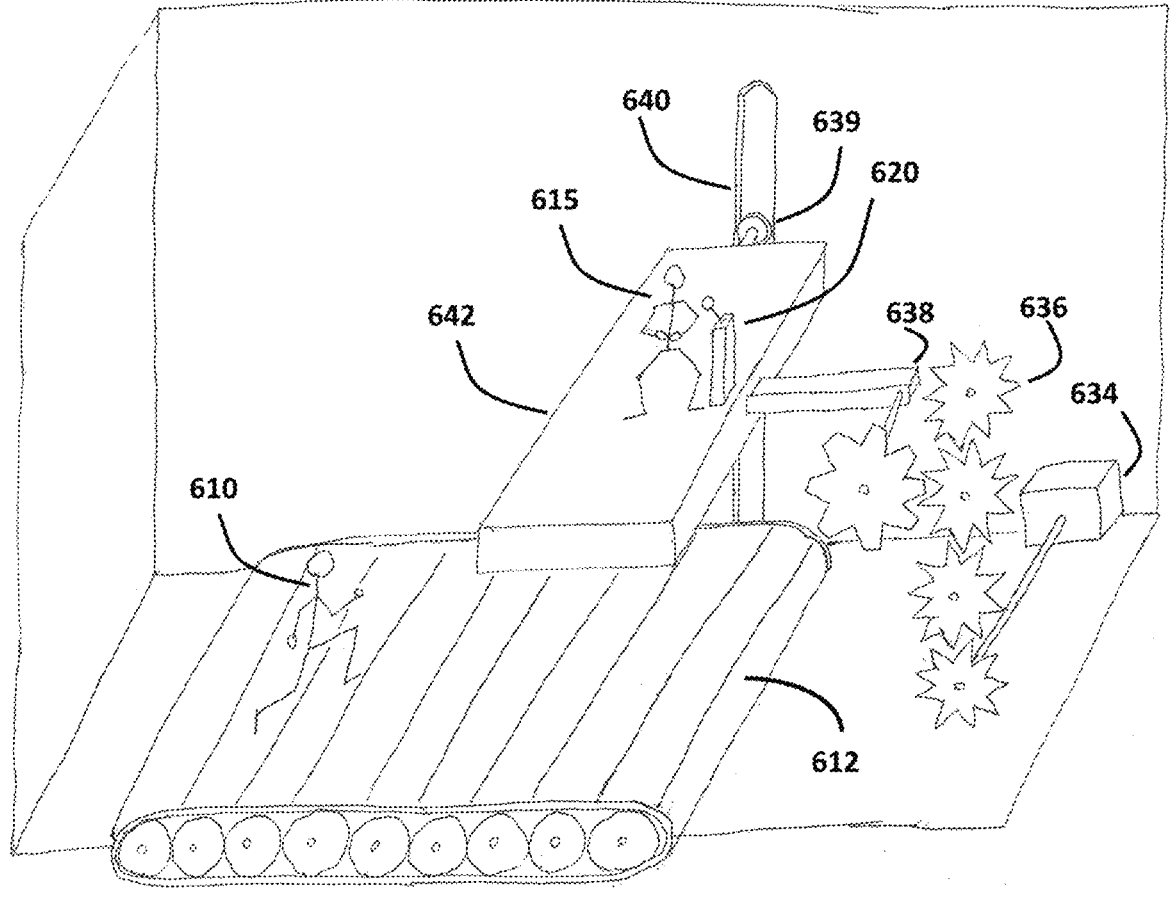
FIG. 14 illustrates a room with a moving walkway spanning its width and length beneath platform which may be raised and lowered by a system of motors, gears, guides, and pulleys, located in the walls and adjacent rooms.

As illustrated in FIG. 14 another embodiment of the disclosure may relate to a room with a user, 610, moving on a treadmill, 612 spanning the room's width, portions of said treadmill being beneath a platform which spans part of the same area. In some variations this platform may be raised and lowered at the behest of an observer, 615, in some instances it may be in response to the observer depressing of a tactile sensor relay, 620. The platform may be moved by a system containing any number of motors, 634, gears, 636, guides, 638, 639, and pulleys, 640. In other variations this platform, 642, may be stationary and slightly above the treadmill, and accessible ladder. In other variations the treadmill may stop once the added weight of the platform is loaded on to it. Then the treadmill may start up again once the platform raises and the observer is safely above the treadmill.

Figure 15:
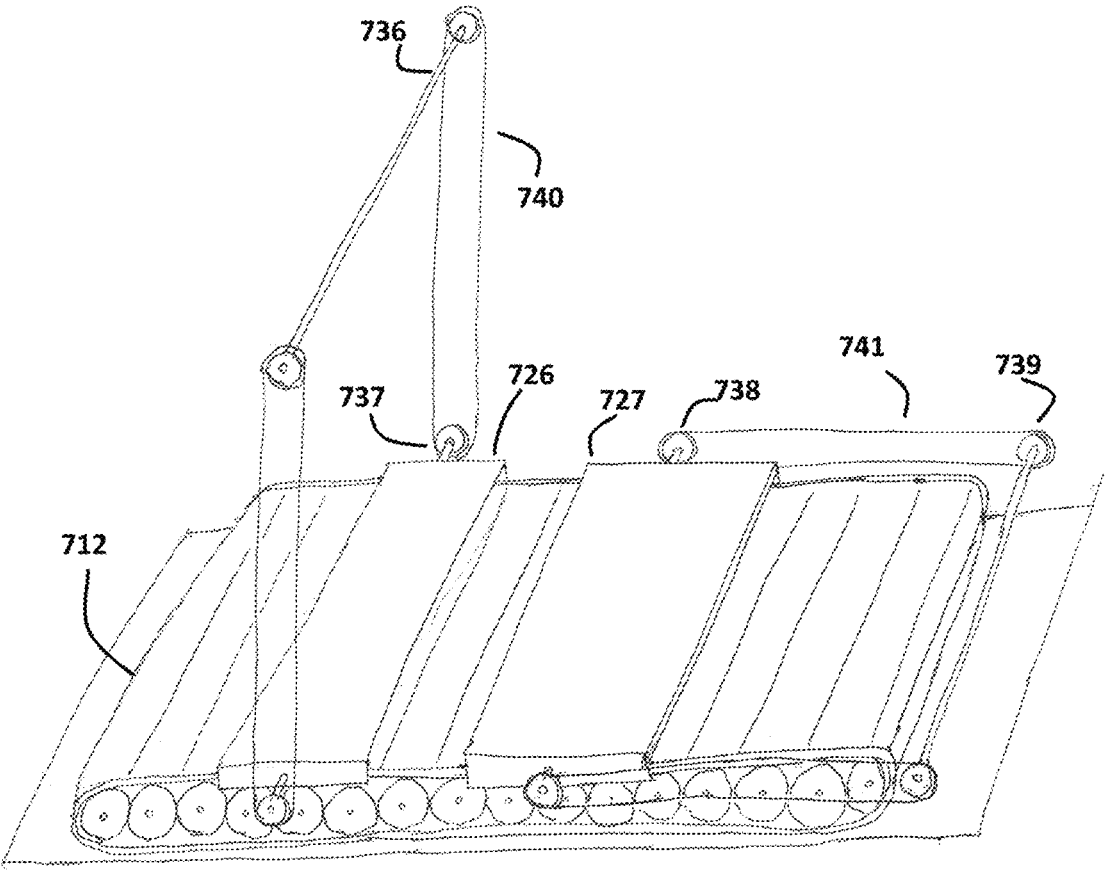
FIG. 15 illustrates a room with a moving walkway spanning its width and length, beneath a plurality of platforms moving in various directions.

As illustrated in FIG. 15 other embodiments may involve a moving walkway, 712, spanning the length and width of the room, beneath a plurality of platforms, moving in various directions, including vertical, 726, and horizontal, 727. These platforms may be guided by a system of motors, gears, guides, 738, 739, and pulleys, 740, 741 moving an axis connected to the platform in a desired direction. This room may be used for a variety of purposes, including but not limited to a simulation room, game room, or obstacle course.

Figure 16:
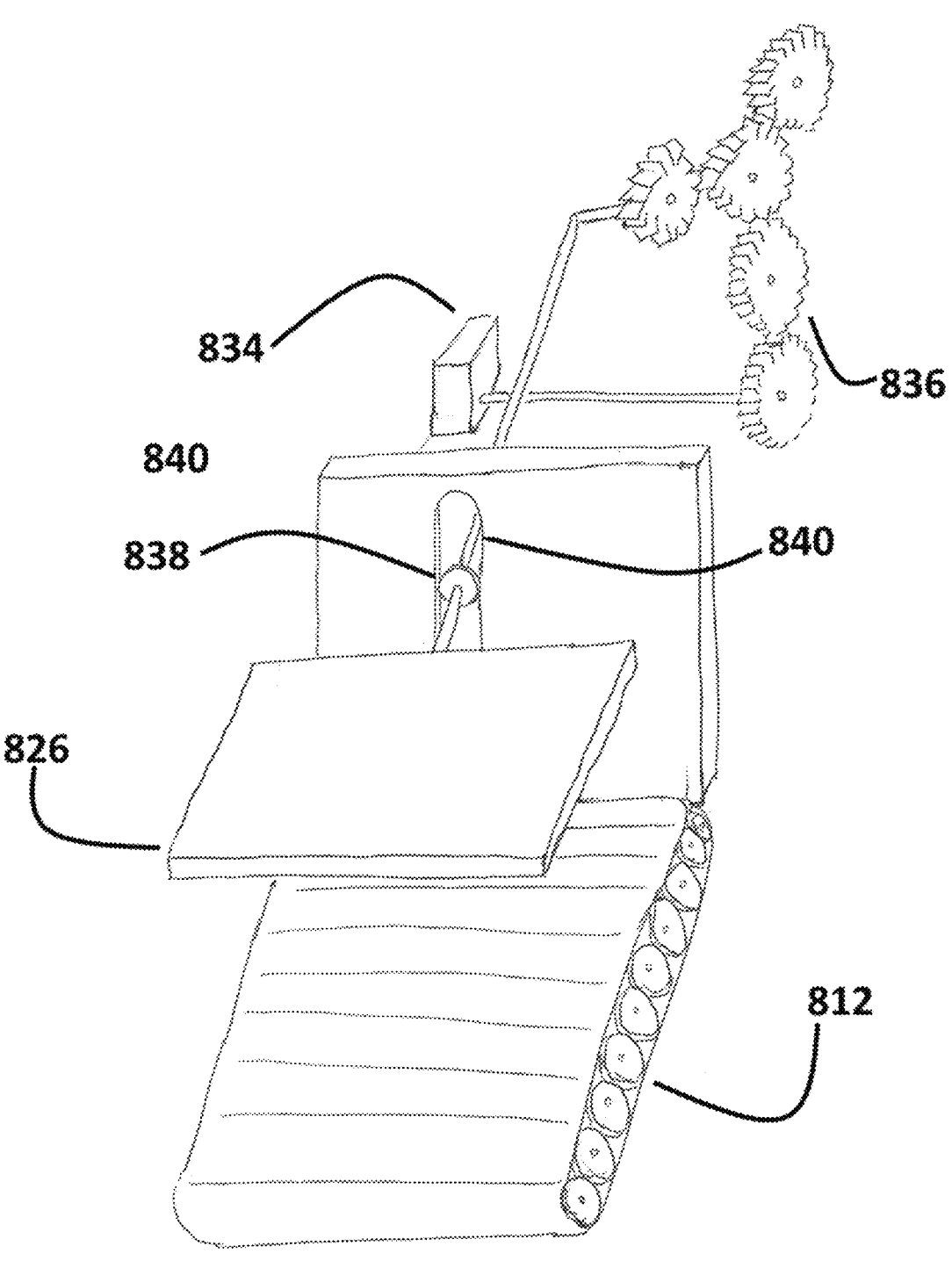
FIG. 16 illustrates a cross-sectional orthogonal view of a room containing a platform which may raise and lower to start and stop the moving walkway.

As illustrated in FIG. 16 certain embodiments may contain a treadmill, 812 spanning its width and length, said walkway being beneath a platform, 826 which spans part of the same area. In some variations this platform may be raised and lowered by a system of motors, 834, gears, 836, guides, 838, 839, and pulleys, 840, located in the walls and adjacent rooms. In some variations this platform may raise to nearly the height of the ceiling automatically.

Figure 17:
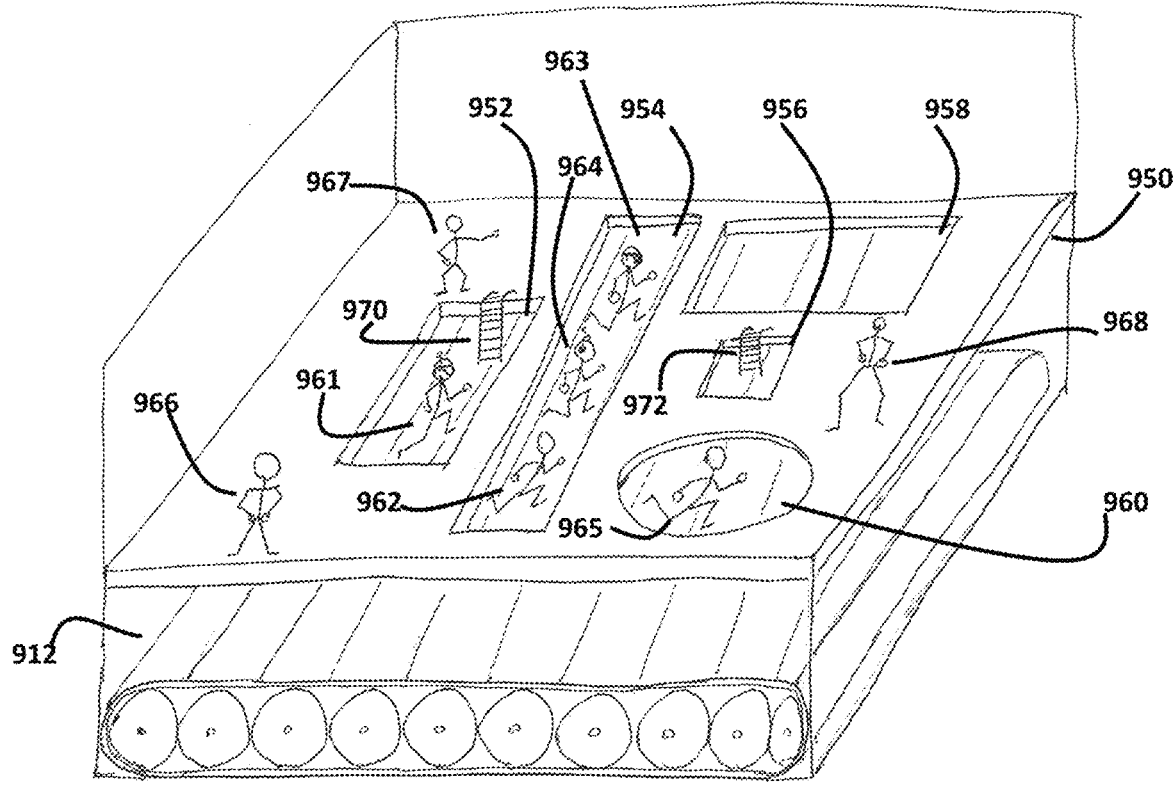
FIG. 17 illustrates room with a moving walkway spanning its entire length and width, and a floor at an elevation above said moving walkway, the floor containing a plurality of holes, large enough for users to enter.

As illustrated in FIG. 17 other embodiments may involve a room comprising a moving walkway, 912, spanning its entire length and width, and a floor, 950 at an elevation above said moving walkway, the floor containing a plurality of holes, 952, 954, 956, 958, 960, large enough for a plurality of users, 961, 962, 963, 964, 965 to enter while being monitored by one or more observers, 966, 967, 968. Variations of this embodiment may involve holes of various sizes, for different user arrangements. Other variations may involve holes with ladders, 970, 972, for users to access said holes.

Figure 18:
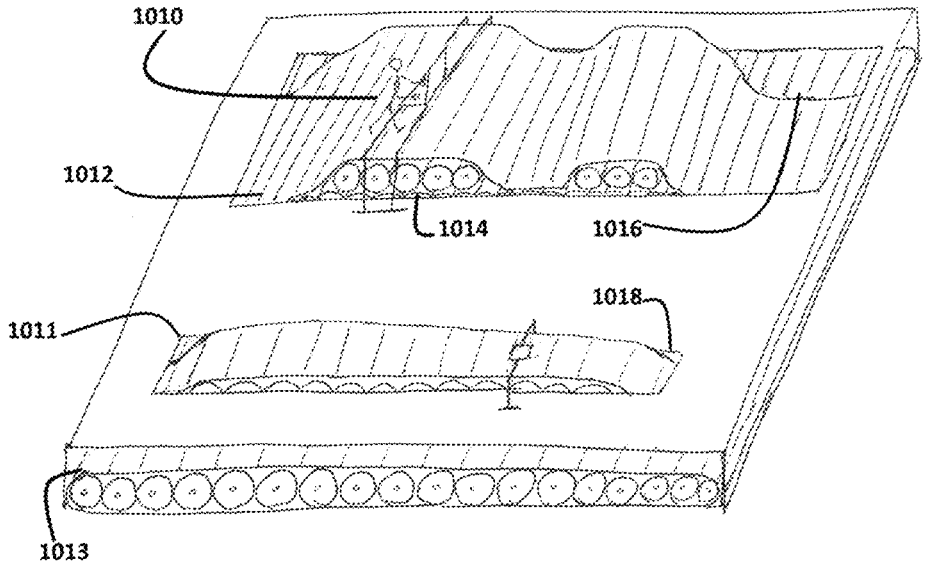
FIG. 18 illustrates room with a moving walkway spanning its entire length and width, with rollers stacked beneath select widths of moving walkways with more pallets than adjacent portions of moving walkways, placed directly within holes in a floor located above all portions of the moving walkway which are not directly beneath said holes.

As illustrated in FIG. 18 in other embodiments users, 1010, may move on raised portions, 1011, 1012 of a treadmill, 1013, spanning the room's length and width, with rollers, 1014, stacked beneath select widths of the treadmill, fitting between holes, 1016, 1018, in a floor above all unraised portions of said treadmill. In some variations raised portions of the treadmill may be level with the elevation of the floor, while in other variations it may be lower or higher. These variations may allow for advantages including but not limited to safety of dismounting, ease of building, and aesthetics.

Figure 19:
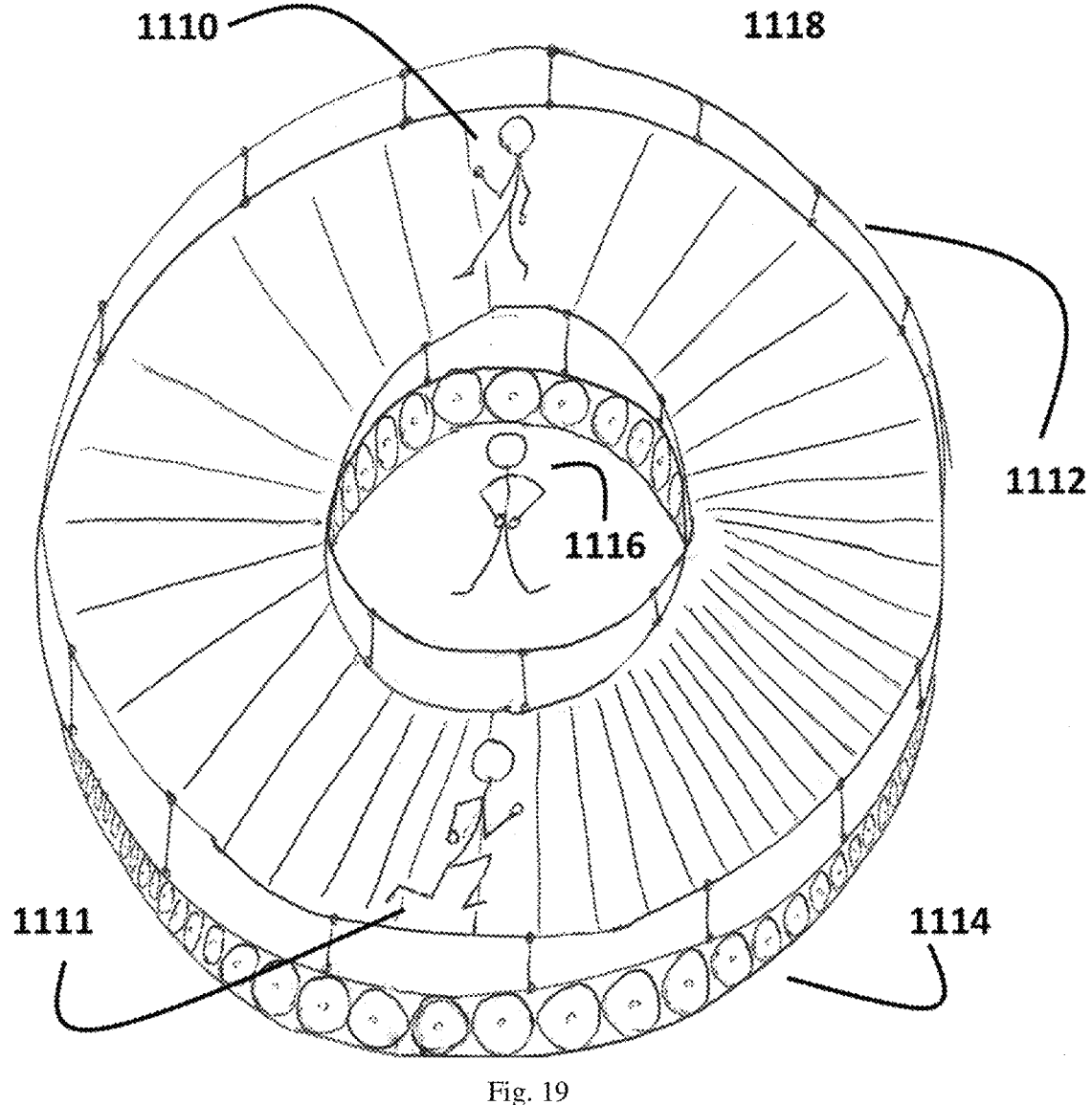
FIG. 19 illustrates an area with a circular treadmill, guided by a system of rollers wherein said treadmill is in use by a plurality of users.

As illustrated in FIG. 19, another embodiment of this disclosure may involve an area with a plurality of users, 1110, 1111, on a circular treadmill, 1112, guided by a system of rollers, 1114, as an observer, 1116, watches. In some variations users may be assisted in movement and prevented from falling out by means including but not limited to guide rails, 1118.

Figure 20:
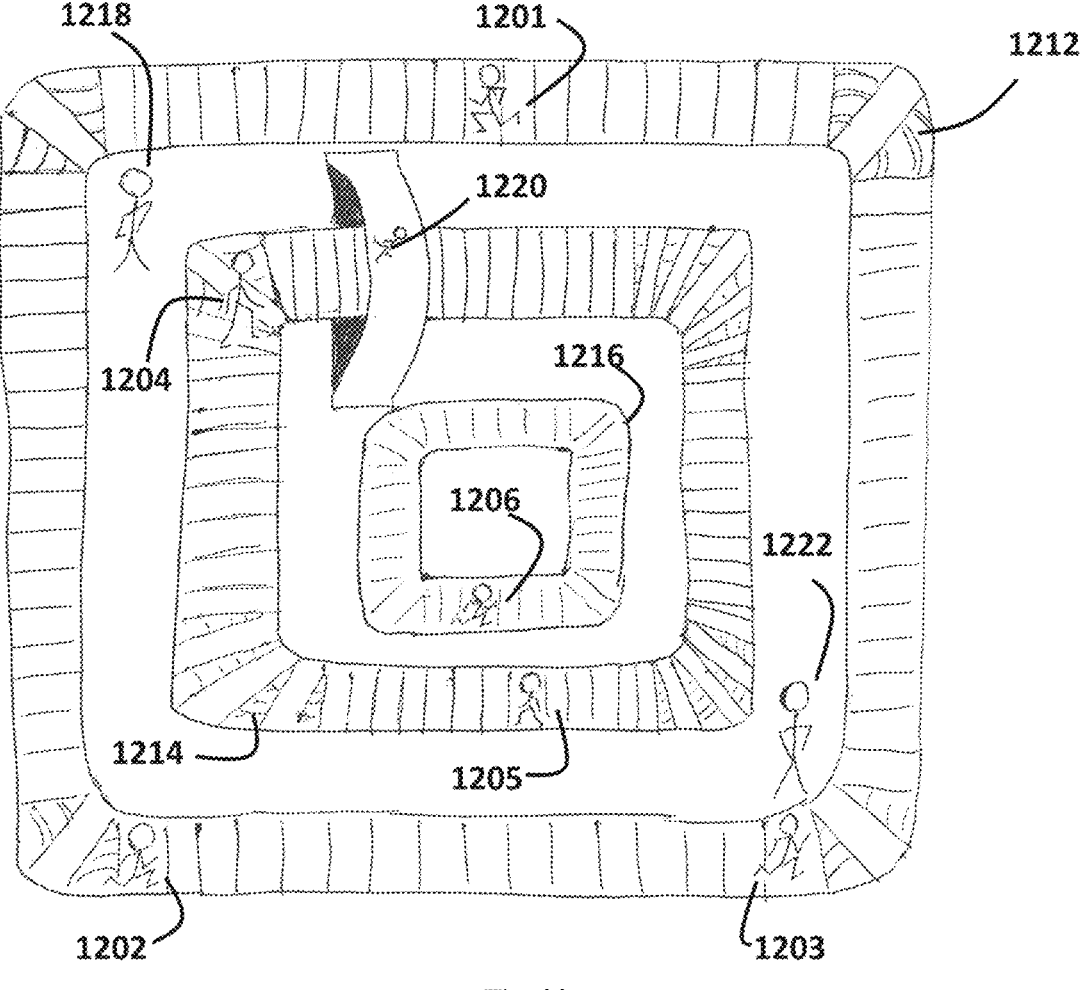
FIG. 20 illustrates an area with a plurality of users on a plurality of moving walkways, arranged in a concentric pattern, while a plurality of observers stand outside of the moving walkways on land in between or above said moving walkways.

As illustrated in FIG. 20 other embodiments may involve a plurality of users, 1201, 1202, 1203, 1204, 1205, 1206 on a plurality of moving walkways, 1212, 1214, 1216 arranged in a concentric pattern, while a plurality of observers, 1218, 1220, 1222 stand outside of the moving walkways, on land in between or above said moving walkways. In certain variations the users or observers would be able to control the speed of certain moving platforms.

Figure 21:
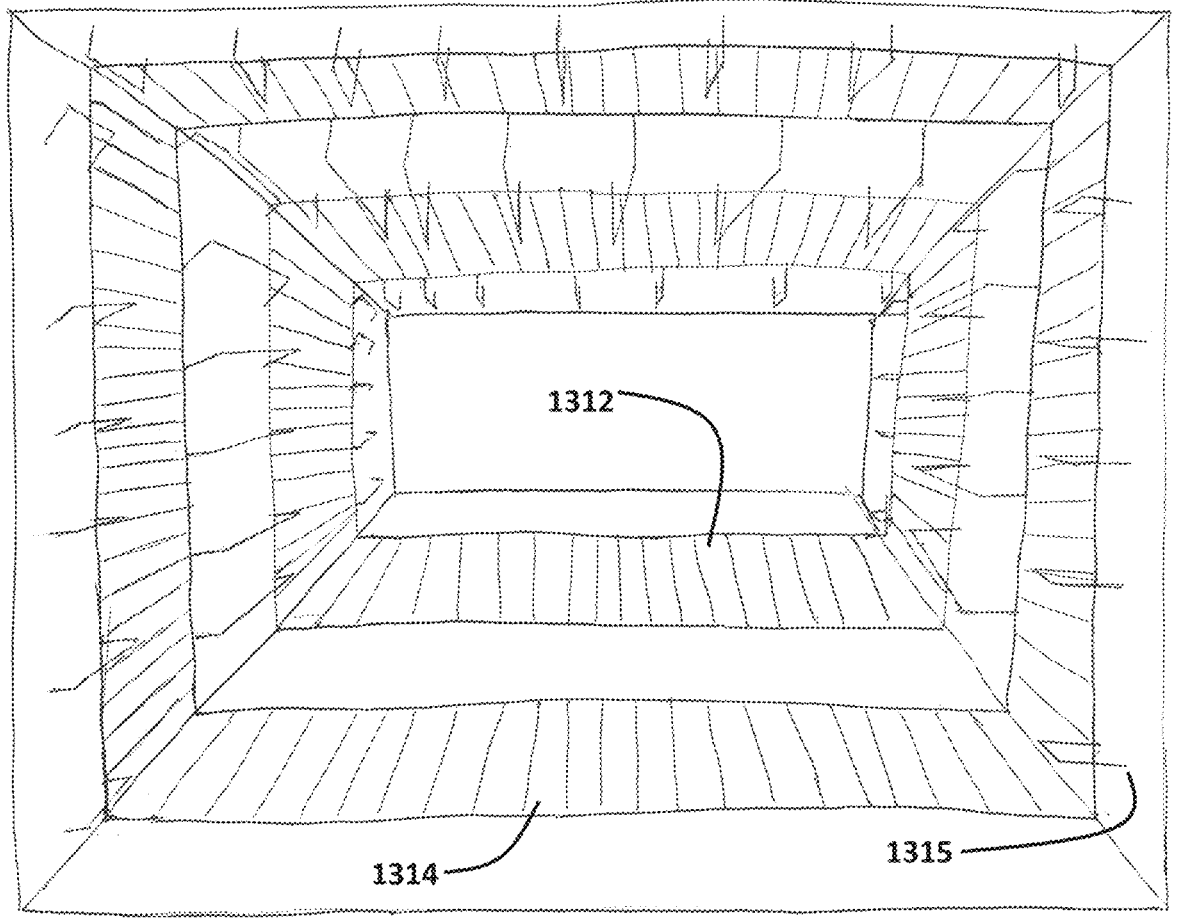
FIG. 21 illustrates a room with a plurality of moving walkways revolving the width of the room from the floor to the ceiling, and staggered handlebars for a user to traverse the room in a direction the same as or opposite of the moving walkway.

As illustrated in FIG. 21 another embodiment may involve a plurality of moving walkways, 1312, 1314 revolving the width of the room from the floor to the ceiling, and staggered handlebars, 1315 for a user to traverse the room in a direction the same as or opposite of the moving walkway.

Figure 22:
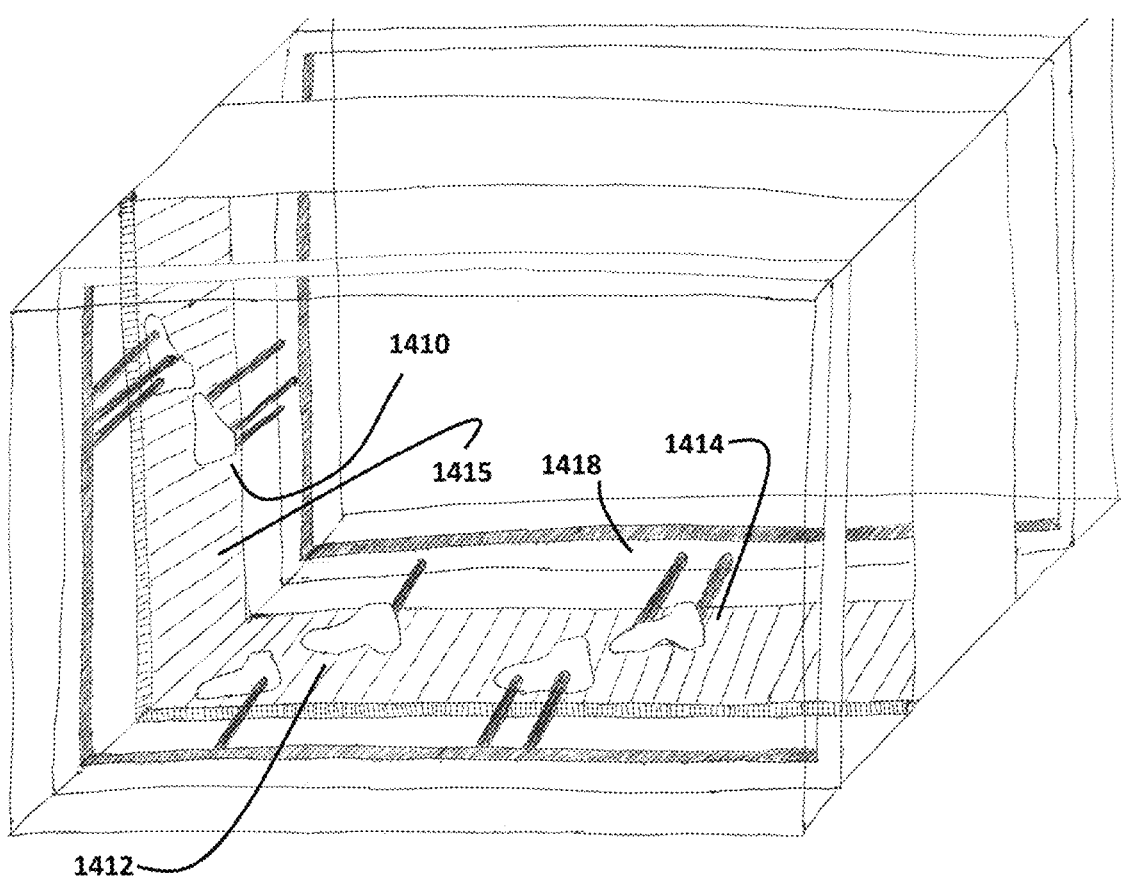
FIG. 22 illustrates a room with a plurality of users traversing a moving walkway revolving the width of the room from the floor to the ceiling, said room containing floor guides with shoe attachments to aid the user in revolving the room.

As illustrated in FIG. 22 yet another embodiment may involve a room with a plurality of users, 1410, 1412, 1414, traversing a moving walkway, 1415, revolving the width of the room from the floor to the ceiling, said room containing floor guides with shoe attachments, 1418, to aid the user in revolving the room. In some variations these shoe attachments may be elastic to help the user walk around without falling from the floor guides. In other variations the users' walking may be further supplemented in their endeavors to walk the ceiling by magnetic boots, which allow a user to step on a moving walkway, where the floor pallets are metal.

Another embodiment of this disclosure may be a method for teaching students utilizing one or more treadmills or moving walkways to present educational material to one or more students while said students are in motion. In some variations, the treadmill or moving walkway may span the majority of the floor of the classroom. In other variations, the classroom may have one or more treadmills or moving walkways assigned to individual students. In other variations, the students may be fitted with sensor relays that monitor and relay information on one or more attributes related to the user's movement such as pulse, speed, or fatigue.

In another embodiment, users may be fitted with headsets or displays at their individual workstations. Said headsets or displays may be used to present learning material. An advantage of the described teaching method may be utilizing the effects of movement to increase concentration, focus, and attention span. Another advantage of the described teaching method may to promote regular exercise and multitasking.

Figure 23:
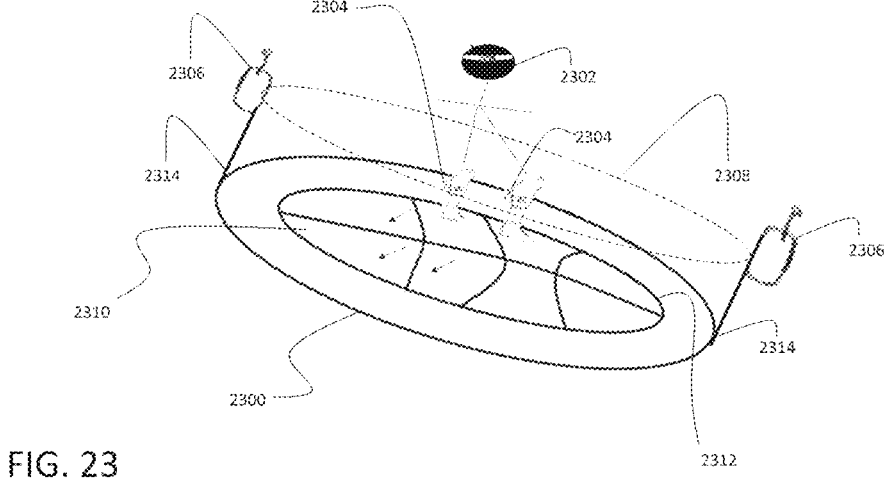
FIG. 23 illustrates a movement device, in this case an omni directional walkway, where the area is bound by sensor relays which communicate with the sensors the user is wearing to determine how to adjust the velocity of the omni-directional walkway to keep the user from walking out or inform them on their output device they are getting close to exiting, or alerting the user in other ways.

As illustrated in FIG. 23 yet another exemplary embodiment may involve a moving device 2300 for use by one or more users 2302 who may be fitted with one or more sensor relays 2304, which may transmit signals to and from sensor relays 2306 associated with the movement device, such that they may form an electromagnetic perimeter 2308 around the unit by means including but not limited to photo-eye sensors, laser alignment sensors, proximity sensors or magnetic field. In some such embodiments these sensor relays may be used to direct the movement of the motion device, in this example a trackpad 2310 that gradually descends to a stable platform 2312, on which sensor relays are attached around the perimeter of the movement device at one or more points 2314. The sensor relays around the perimeter may be used for a variety of features including but not limited to sensing the user's proximity to the perimeter, the user's speed, the user's velocity in comparison with the track-pad, the readings sent from an output device, sending a signal to adjust the trackpad, sensing if the user has breached the perimeter, sensing if the sensor relays have breached the perimeter, sensing if the user has jumped, or sensing if the user has entered or breached any manufacturer or user set parameters.

Figure 24:
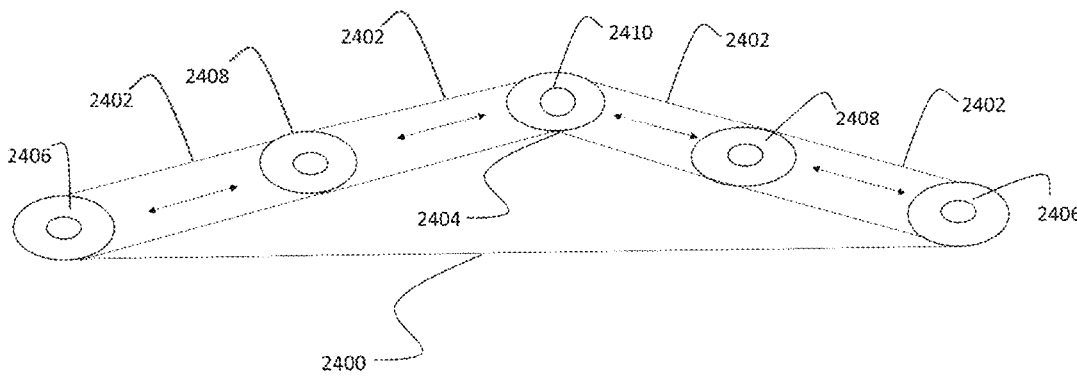
FIG. 24 illustrates a movement device, in this case a multidirectional walkway, where rollers are used to move a conveyor belt. In some embodiments these rollers may be bound by the belt hoisted on an elevating platform which can change angles. In some such embodiments where this is combined with a sensor relay system, the belt could change velocity (or direction or speed independently) in response to the users detected movements or signals transmitted from an output device.

As illustrated in FIG. 24 yet another exemplary embodiment may involve a movement device 2400, where a trackpad 2402 is propelled forward or in reverse by a plurality of rollers at its base 2406, possibly at intermediate elevations 2408, and possibly at its zenith 2410, propelled by means including but not limited to motors, levers, or magnetic activation, where rollers at an elevation by an adjustable base 2404, which may adjust angles, propelled by means including but not limited to motors, levers, or magnetic activation.

Figure 25:
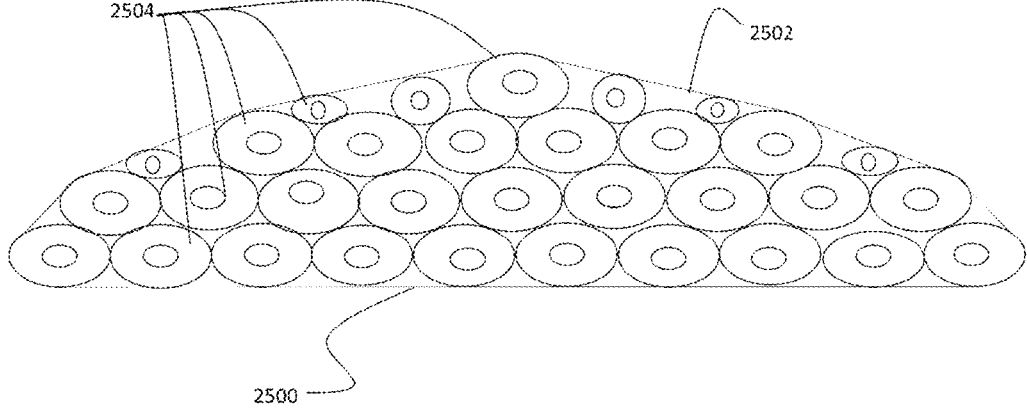
FIG. 25 illustrates a movement device, in this case a multidirectional directional walkway, which can be bound by sensor relays in some embodiments. A plurality of rollers are shown within the movement device, which are touching each other and the belt so that their velocity/acceleration can be altered in unison while altering the velocity/acceleration of the belt.

As illustrated in FIG. 25 yet another exemplary embodiment may involve a movement device, 2500, comprising a moving walkway or track-pad, 2502, rotating around the movement device as it is propelled by a plurality of attached rollers, 2504.

Figure 26:
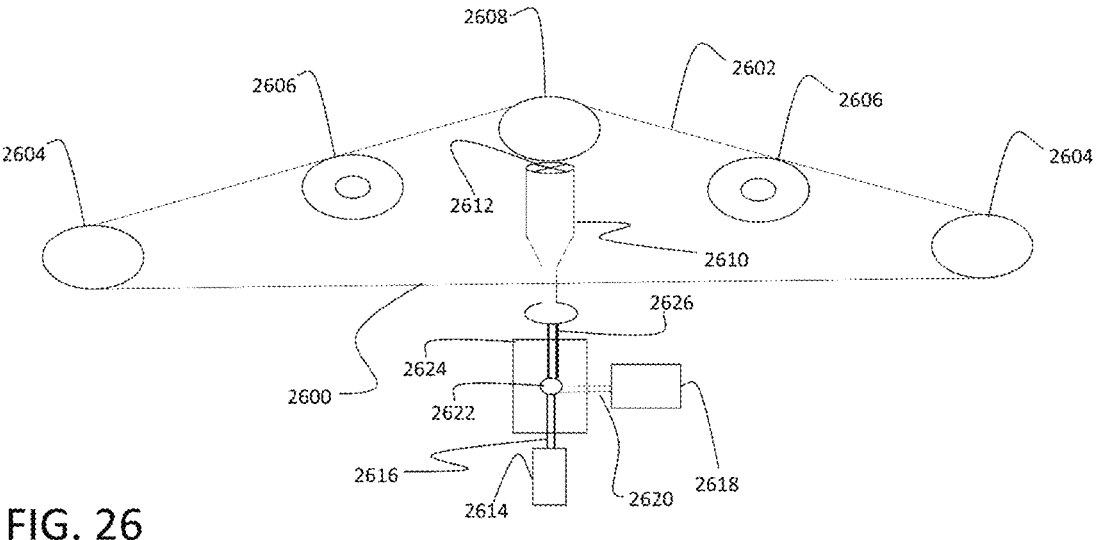
FIG. 26 illustrates a movement device, in this case an omni directional walkway, where direction and spin of the movement device's walkway can be driven by a pivot arm controlled by one or more motors.

As illustrated in FIG. 26 yet another exemplary embodiment may involve a movement device, 2600, comprising a moving walkway or track-pad, 2602, rotating around the movement device as it is propelled by one or more rollers, 2606, one or more balls, 2604, or some combination therein. In the illustrative example am abrasive ball 2608, at the movement device's zenith, is used to propel the trackpad above it, as it is turned from below by the abrasive surface 2612 of a pivot arm 2610, which may be moved or rotated by a rod 2626 that is driven by one or more motors 2614, 2618, the shafts of which 2616, 2620 rotate a pivot ball 2622, held in an enclosure 2624, wherein the pivot ball is attached to the stems and the rod, thereby controlling the spin, or angle of the pivot arm and thereby the trackpad.

Figure 27:
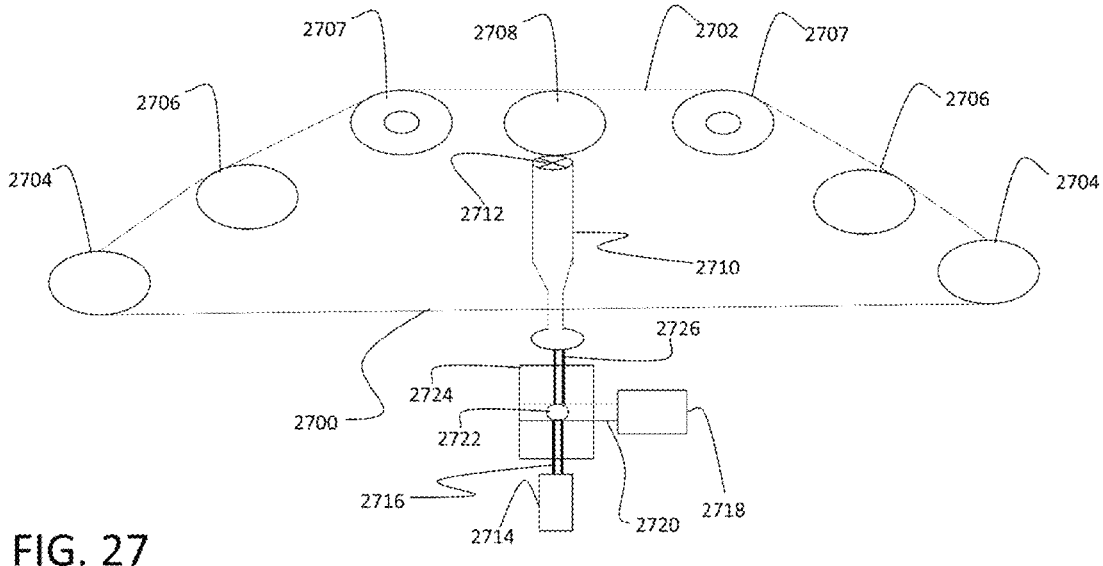
FIG. 27 illustrates a movement device, in this case an omni directional walkway, where direction and spin of the movement device's walkway can be driven by a pivot arm controlled by one or more motors, and in which rollers and balls are located at a plurality of elevations for ergonomic transition angles from the top of the walkway to the lowest traversable point to be achieved.

As illustrated in FIG. 27 yet another exemplary embodiment may involve a movement device, 2700, comprising a moving walkway or track-pad, 2702, rotating around the movement device as it is propelled by one or more rollers, 2707, one or more balls which may be at the base, 2704, or at a supporting elevation 2706, or the controlling ball 2708 which is propelled and turned from below by the abrasive surface 2712 of a pivot arm 2710, which may be moved or rotated by a rod 2726 that is driven by one or more motors 2714, 2718, the shafts of which 2716, 2720 rotate a pivot ball 2722, held in an enclosure 2724, wherein the pivot ball is attached to the stems and the rod, thereby controlling the spin, or angle of the pivot arm and thereby moving or spinning the trackpad.

Figure 28:
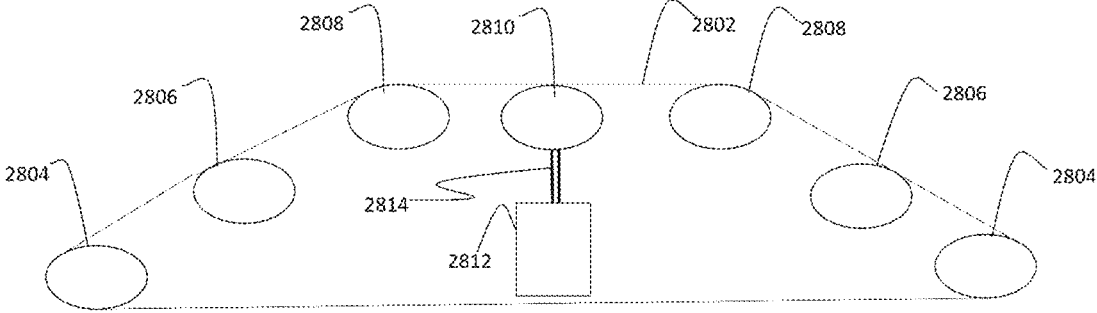
FIG. 28 illustrates a movement device, in this case an multi-directional walkway, where the spin of the movement

As illustrated in FIG. 28 yet another exemplary embodiment may involve a movement device, 2800, comprising a moving walkway or track-pad, 2802, rotating around the movement device as it is propelled by one or more balls which may be at the base 2804, at a supporting elevation 2806, at a location 2808 parallel to the elevation of the controlling ball 2810 which is propelled and turned from below by a motor 2812, and its shaft 2614 which may be attached to and spin the ball (and thereby the trackpad) in some such embodiments.

As illustrated in FIG. 29 yet another exemplary embodiment may involve a movement device, 2900, comprising a moving walkway or track-pad, 2902, rotating around the movement device as it is propelled by one or more rollers, 2907, one or more balls which may be at the base, 2904, or at a supporting elevation 2906, or the controlling ball 2908 which is propelled and turned from below by the abrasive surface 2912 of a pivot arm 2910, which may be moved by a rod 2926 that is driven by one or more motors 2918, the shaft of which 2920 rotates a pivot ball 2922, held in an enclosure 2924, wherein the pivot ball is attached to the stems and the rod, thereby controlling the angle of the pivot arm and thereby moving the trackpad.

As illustrated in FIG. 30 yet another exemplary embodiment may involve a movement device, 3000, comprising a moving walkway or track-pad, 3002, rotating around the movement device as it is propelled by one or more rollers, 3007, one or more balls which may be at the base, 3004, or at a supporting elevation 3006, or the controlling ball 3008 which is propelled and turned from below by the abrasive surface 3012 of a pivot arm 3010, which may be moved by a rod 3026 that is driven by a plurality of motors 3018, 3022, the shaft of which 3020 rotates a pivot ball, held in an enclosure 3024, wherein the pivot ball is attached to the stems and the rod, thereby controlling the angle of the pivot arm in a plurality of directions and thereby moving the trackpad.

As illustrated in FIG. 31 yet another exemplary embodiment may involve a movement device, 3100, comprising a moving walkway or track-pad, 3102, rotating around the movement device as it is propelled by one or more rollers, 3108, one or more balls which may be at the base, 3104, or at a supporting elevation 3106, or the controlling ball 3110 which is propelled and turned from below by a rod 3112 that is driven by one or more motors 3122, 3118, the shaft of which 3120 rotates a pivot ball, held in an enclosure 3124, wherein the pivot ball is attached to the stems and the rod, though the rod exits the enclosure at 3126, thereby controlling the angle of the pivot arm and thereby moving the trackpad.

As illustrated in FIG. 32 yet another exemplary embodiment may involve a movement device with a stable platform, 3200, comprising a moving walkway or track-pad, 3202, rotating around the movement device as it is propelled by one or more rollers, 3207, one or more balls which may be at the base 3226, the widest point, 3204, or at a supporting elevation 3206, or the controlling ball 3208 which is propelled and turned from below by the abrasive surface 3212 of a pivot arm 3210, which may be moved by a rod 3226 that is driven by a plurality of motors 3218, 3222, the shaft of which 3220 rotates a pivot ball, held in an enclosure 3224, wherein the pivot ball is attached to the stems and the rod, thereby controlling the angle of the pivot arm in a plurality of directions and thereby moving the trackpad.

As illustrated in FIG. 33 yet another exemplary embodiment may involve a movement device with a stable platform, 3300, comprising a moving walkway or track-pad, 3302, rotating around the movement device as it is propelled rollers, 3307, one or more balls of which may be at the base 3326 and propelled by motors 3310, 3320 which spin stems 3312, 3322 controlling the rotation of bearings or rollers 3314, 3324 and thereby the balls thereby controlling the angle of the pivot arm in a plurality of directions and thereby moving the trackpad, the widest point, 3304, or at a supporting elevation 3306, or a ball in the center of the platform 3308.

As illustrated in FIG. 34 yet another exemplary embodiment may involve a movement device with a stable platform, 3400, comprising a moving walkway or track-pad, 3402, rotating around the movement device as it is propelled by one or more rollers, 3407, one or more balls which may be at the base 3426, the widest point, 3404, or at a supporting elevation 3406, or the controlling ball 3408 which is propelled and turned from below by a rod 3426 that is driven by a plurality of motors 3418, 3422, the shaft of which 3420 rotates a pivot ball, held in an enclosure 3424, wherein the pivot ball is attached to the stems and the rod, thereby controlling the angle of the pivot arm in a plurality of directions and thereby moving the trackpad.

As illustrated in FIG. 35 yet another exemplary embodiment may involve a movement device with a stable platform, 3500, comprising a moving walkway or track-pad, 3502, rotating around the movement device at alternating velocities in response to user movement allowing the user to pace along the moving walkway or trackpad for an extended period of time.

As illustrated in FIG. 36 yet another exemplary embodiment may involve a movement device with a stable platform, 3600, comprising a moving walkway or track-pad, 3602, spinning around the movement device, allowing the user walk in a circular pad around the trackpad without necessarily moving in relationship to the stable platform.

As illustrated in FIG. 37 yet another exemplary embodiment may involve a movement device, 3700, comprising a moving walkway or track-pad, 3702, rotating around the movement device as it is propelled by one or more rollers, 3706, one or more balls, 3704, or some combination therein. In the illustrative example an abrasive ball 3708, at the movement device's zenith, is used to propel the trackpad above it, as it is turned from below by the abrasive surface propelled by motors 3712 which spin stems 3714 controlling the rotation of bearings or rollers 3716 and thereby the balls thereby controlling the angle of the pivot arm in a plurality of directions and thereby moving the trackpad.

As illustrated in FIG. 38, another exemplary embodiment may involve an apparatus, 3820, comprising a circular track or moving walkway, 3822, with supports, 3824, for handle bars, 3826, which in certain embodiments may be powered by a battery, 3828, which may be wired, 3829, to the system, or a solar panel, 3830, which may be wired, 3832, to the system to supply power. In some variations of the embodiment, the apparatus may be supplemented by a canopy pole, 3834, attached to an overhead canopy, 3836, which can be comprised of solar panels, which can also be present in side panels and used to display images on the display panels, 3838, (which may be directly over top of the solar panels, allowing just enough light to pass through to power the display, or charging a battery to do so at a time when enough light cannot pass through to power it) including false images as collected by any number of cameras, 3840, connected via a wire, 3842, or wirelessly to a display panel. In this exemplary embodiment a tent 3844 can be mounted above the system for benefits including added shade; concealment, through a false-images being recorded on any number of cameras, 3846, and displayed on a display monitor; protection from the elements; and additional solar absorption through panels comprising the tent, 3848.

As illustrated in FIG. 39, another exemplary embodiment may involve a user 3914 wearing one or more output device(s) 3916 and one or more sensor relays 3902 that is given and receives feedback from a plurality of sensor relays 3904, 3906, 3908, 3910 forming a perimeter about an area 3912. In some embodiments the user's output device may be mixed reality, augmented reality or virtual reality lenses which may show images of walkways 3918 and exercise equipment to aid the user. In some such exemplary embodiments the sensor relay may indicate when the user has exited a perimeter marked by electromagnetic signals sent between other sensor relays located at the boundaries of the perimeter. In some such exemplary embodiments the sensor relay may then send one or more signals to the user's visual headset interrupting the movie the user was watching on it to tell them they are outside of a designated safe pacing zone.

As illustrated in FIG. 40, another exemplary embodiment may involve a user 4014 wearing one or more output device(s) 4016 and one or more sensor relays 4002 that is given and receives feedback from a plurality of sensor relays 4004, 4006, 4008, 4010 forming a perimeter about an area 4012. In some embodiments the user's output device may be mixed reality, augmented reality or virtual reality lenses which may show images of walkways 4018 and exercise equipment to aid the user and/or the images could be created/augmented by means including but not limited to a projector 4022, using a lens 4020 to aim light containing an image 4024 (as shown) laser display, or holographic image. In some such exemplary embodiments the sensor relay may indicate when the user has exited a perimeter marked by electromagnetic signals sent between other sensor relays located at the boundaries of the perimeter. In some such exemplary embodiments the sensor relay might then send one or more signals to the user's visual headset interrupting the movie the user was watching on it to tell them they are outside of a designated safe pacing zone.

As illustrated in FIG. 41, another exemplary embodiment may involve a modular walkway 4100, connecting a series of trackpads 4102 such that their routes 4114 may be linked together 4114 as it is driven by a series of rollers 4114. The walkway supports or barriers 4104 may raise 4106 and lower 4108 as needed in some embodiments for the user to exit. In some such exemplary embodiments the trackpads may be reversible, adjust velocity in relationship to a user's movement or performance, or any combination therein.

As illustrated in FIG. 42, another exemplary embodiment may involve a movement device 4200, in this case a multi-directional walkway (here being illustrated as a transparent belt covering the other components like a tarp) 4202, where in some exemplary embodiments a ball in the middle 4204 may be used to drive the direction of the belt, as the belt glides over the rollers 4208 at a plurality of locations, including bending under those along the perimeter 4206. In other exemplary embodiments the rollers along the perimeter may be attached to motor stems to drive the direction of the walkway.

As illustrated in FIG. 43, another exemplary embodiment may involve a movement device 4300, in this case an omni-directional walkway (here being illustrated as a transparent belt covering the other components like a tarp) 4302, where in some exemplary embodiments a ball in the middle 4304 may be used to drive or spin the direction of the belt, as the belt glides over the rollers 4306, balls 4308 and combinations 4310. In other exemplary embodiments the rollers along the perimeter may be attached to motor stems to drive the direction of the walkway.

As illustrated in FIG. 44, another exemplary embodiment may involve a movement device 4400, in this case an omni-directional walkway (here being illustrated as a transparent belt covering the other components like a tarp) 4402, where in some exemplary embodiments a ball in the middle may be used to drive or spin the direction of the belt, as the belt glides over a plurality of balls 4406 for ease of directional change as it rotates around the perimeter.

As illustrated in FIG. 45, another exemplary embodiment may involve a movement device 4500, in this case an omni directional walkway 4508, where the area is bound 4504 by sensor relays 4502 which in some exemplary embodiments may communicate with sensors the user 4506 is wearing to determine how to adjust the velocity of the omni-directional walkway to keep the user from walking out or inform them on their output device they are getting close to exiting, or alerting the user in other ways and the walkway traverses is spherically shaped.

As illustrated in FIG. 46, another exemplary embodiment may involve a movement device 4600 comprising a sphere 4608 bound to several movement pads, including but not limited to stationary pads, or in this illustrative case modular walkways 4604, combinable 4606 such that their route may be linked together as it is driven by a process including but not limited to the mechanical connections, a series of driven rollers, balls or clips. In some embodiments the modular walkways may have supports or barriers 4602 that in some such embodiments, that may raise and lower as needed in some embodiments for the user to exit.

As illustrated in FIG. 47, another exemplary embodiment may involve a movement device 4700, in this case an omni directional walkway 4712, where the area is monitored by one or more sensor relay(s) 4702 which communicate 4704 with the sensors 4706 the user 4710 is wearing to determine how to adjust the velocity of the omni-directional walkway which may move or spin in a plurality of directions 4714 to keep the user from walking out or inform them on their output device 4708 they are getting close to exiting, or in some exemplary embodiments alerting the user in other ways, which further includes sensors 4716 for detecting the force of the users weight such that if a user steps off or jumps up from the walkway it can be detected and a signal sent to the movement device or user or an observer's media device or other output device.

As illustrated in FIG. 48, exemplary embodiments may involve students on movement devices, 4806, while utilizing educational software via headsets, including but not limited to augmented reality, mixed reality or virtual reality headsets and AV devices or sensors monitoring or allowing teachers 4802, 4808, 4818 and 4826 the ability to monitor users, 4806, 4812, 4824, in some embodiments the output device or exercise devices collecting solar energy through a panel, 4800, 4808, 4814, or backup battery, 4816, or some combination therein to enhance performance. Users and teachers may receive alerts through the database as shown by the illustrative explanation marks on the user's headsets, 4808, 4824.

As illustrated in FIG. 49, exemplary embodiments may educational software monitoring the users' performance and responding to their movements in fun ways. In some such embodiments this may be displayed for users in ways including but not limited to a GUI interface for users on a cell phone application 4900, on a computer screen or in a virtual reality, augmented reality, or mixed reality application.

FIG. 50 is an exemplary embodiment following a standard Internet architecture in which one or more user's output devices 5024 and a server 5000 are connected via the internet/wireless network 5022 and modems 5026, 5020 or other communications channels. A user accesses the server 5000 via their output device or movement device 5024 potentially via their performance on said device or via direct verbal commands operating a web browser 5030 or other software application residing in RAM memory 5008 that allows it to display information downloaded from a server 5000. The server system 5000 runs server software 5014, including the classroom operating software 5016 of the present invention, which interacts with the output device/ sensor relay 5024 and a user information database 5002. The database 5002 contains data regarding individual user performance collected via sensors, data regarding overall class performance measured by sensors, data regarding the users collected by sensors on the user, data from the users collected by user input, prerecorded data or some combination therein. The classroom operating software 5016 in some situations will process a user's verbal commands by acting in means including but not limited to pulling information from the database 5002 adding information to it, sending information back to the device such it can respond verbally to the user in language they will understand. Both the server 5000 and the output device 5024 include respective storage devices, such as hard disks 5006 and 5034 and operate under the control of operating systems 5018, 5032 executed in RAM 5012, 5028 by the CPUs 5004, 5040. The server storage device 906 stores program files 5008 and the operating system 5038. Similarly, the user storage devices 5034 store the inter/intranet browser software 5036 and the operating systems 5038. Typically, the user would utilize the user interface 5042 on their mobile device 5024 but in some such embodiments it may be on the sensor relay itself 5024. In some such exemplary embodiments this system may involve an application which may process a variety of functions including but not limited to vocal commands, changing the lesson plan, increasing the difficulty of the output device or the resistance of a movement device, or letting a teacher know how a student is performing or letting a student know how they are doing in comparison to themselves in the past or others for motivational purposes.

Some embodiments of the present disclosure may be used to implement enhanced in person or remote learning or teaching solutions. This may be accomplished via movement tracking sensors including but not limited to those built into the movement devices, media devices or output devices to track eye or body movement in conjunction with user responses.

In certain embodiments, the introduction of solar panels to the environment may be done in such a way that participants aren't confined to the boundaries of a classroom, treadmill or other relatively limited enclosed space, but instead can actively move around while their movements are being measured utilizing sensors, and their answers to educational tests may be related to said movement. One example of this is an outdoor environment such as a jungle gym simply walking on a field where a student's movement to the left would indicate they believe a particular answer is true, and to the right would indicate they believe a particular answer is false. Inertial measurement software, output devices and movement devices may be used in combination to create a feedback loop for students in an immersive environment, aiding teachers by keeping students occupied and learning while evaluating their own results, as a teacher can monitor their movements, performance or the alerts provided by software to indicate when a student is struggling or in need of assistance.

A series of tests have been identified as a means of determining the effectiveness of some of the solutions to classroom design presented in this disclosure including but not limited to the following:

1) offering methods of delivering high-quality educational content while the participant is engaged in various modes of low intensity repetitive motion. This mode seeks to test the hypothesis that some students will learn better while moving and that movement is beneficial for certain educational outcomes including but not limited to improving memory retention, expanding creative thinking, and enhancing alertness. The need to incorporate movement into education is tied to the belief that doing so will result in beneficial cognitive outcomes.

2) delivering high educational quality content in a consistent structured manner that can be aggregated into a drill that is given and assessed over a given timeline 3) developing a comprehensive framework of interactive systems that deliver high quality educational content, capturing sensory environmental signals given off by the participant, and delivering tailored feedback through leveraging artificially intelligent technologies that provide constructive, instructive correction to the participants in real-time and records his/her reaction to those corrective inputs while measuring the efficacy of that tailored feedback to improve measure of educational proficiency.

It is expected that taken together, these principal modes will create a force multiplier effect driving improved measures of educational proficiency in less time, with less human instruction.

Proposed Experimentation

1. Addition of Small Numbers

This test is designed to isolate and test the second (2) mode—Repetitive Drills. This test will provide some visual educational content that asks the participant each combination of the sum of two numbers from 1 to 5 every drill. Further, instruction will be provided and video will be taken to baseline how effectively and accurately each a group of participants completes this drill. The daily scores of each answer will be aggregated and compared over time until the median number of students in the group answer each question accurately. Results will be compared to a control group of participants that were not engaged in the drilling study, 1a, Alternative Addition of Small Numbers (with movement related feedback) This test is designed to isolate and test the third (3) mode—Artificially intelligent feedback and second (2) mode—Repetitive Drills. In the event that the participants answer the initial question incorrectly a feedback response will be triggered to show a video demonstrating how to add the numbers while using one's fingers to count, and prompt the participants to do so and record the video to confirm or deny compliance and record the accuracy of scores for each of the participants after receiving the instructive feedback. (If proven effective, the compliance of checking to see if the participants follow the prompt to use his/her fingers can be assessed using computer vision applications and demonstrated and in a more automated/scalable method. Furthermore, all participants can be retested days after the initial test with control group measured against the treadmill group and compliant participants measured against noncompliant participants to determine if there is correlation between movement and long-term memory retention.

2. Learning How to Count to Ten in a Foreign Language: This test is designed to isolate and test the first (1) mode repetitive motion. Visual educational content will be delivered to participants demonstrating instruction as to how to count from 1 to 10 in a foreign language. There will be control group who receives the instruction while seated and then asked to demonstrate proficiency after a given time period. For the experimental group, the content will be delivered on a slow-moving treadmill, and then similarly assessed.

3. Measuring Length of Engaged Learning: This test is designed to isolate and test the third (3) mode—Artificially intelligent feedback A software application powered by computer vision will be deployed using video data to classify whether the participant is engaged while, receiving high quality educational content, The application will record the duration of the instruction and educational measures associated with the content and participant to assess the impact of engagement on educational measures of proficiency. The educational content could be teacher led instruction delivered remotely and/or standard educational content and subsequently educational measure could be standardized test scores and/or more specific measures of word recognition/reading comprehension specifically intended to assess the effectiveness of specific educational content.

4. Aggregating learning style and developing models that provide prescriptive feedback. This test is designed to test the first (1) mode—Repetitive Motion the second (2) mode—Repetitive Drills and the third (3) mode Artificially intelligent feedback in concert: The minimum viable product (MVP) envisioned to demonstrate the three multiplier effect of each mode would build on an interactive platform in order to deliver the maximum amount of sensory input that the application might permit, as well as to harvest the maximum amount of response data from the participant. The MVP could be demonstrated on a platform like unity, using inertial measurement sensors, microphones, and computer vision aided video. All of the data collected from the users would be labeled by the participant's response as well as the appropriate/desired response to build a traditional machine learning classifier to identify and suggest the next appropriate interaction with the user. The MVP will require the development of some educational content designed to instruct and assess some specific and measurable competency. It will require the use of at least one sensor capable of recording some key action of the respondent as well as different interactive content that aligns with pre-identified categories of the user. For example, a participant might be asked to identify a picture of a dog, a color, or a word and given a video game controller and/or a speech recognition enabled microphone to record the response. The initial predetermined outcomes might be one for a correct answer, an incorrect answer, a non-answer, and three of the most commonly answered incorrect answers. One of these six responses, in conjunction with a response appropriate for each of the outcomes detected. This example may not require the use of complex ML methods, but one can easily see that over time after collecting sufficient data that deterministic rules written to determine feedback will need to be replaced with complex models used to not only suggest the most impactful piece of feedback, but also to experiment and analyze what that suggestion should be.

5. Alternative Repetitive Motion Feedback Loop-Shuckling to Show Engagement

This test is designed to test the first (1) mode—(Repetitive Motion the third (3) mode—Artificially intelligent feedback: Studies and articles have claimed that movement as simple as fidgeting or shuckling can be done to remove distractions and increase concentration. This test seeks to determine the possibilities of such claims for enhanced concentration. To do so, a control group of participants can be tested for reading comprehension, with one seated and monitored such that they are sitting still while reading passages and answering questions regarding said passages. A test group will be instructed to move around, sway, rock and shake in a repetitive fashion while reading the same passages. These motions will be monitored by a software application with AI monitoring for correlation between movement and performance.

Preferred embodiment of the present disclosure include but are not limited to the following:

1. A system comprising an area containing:
  one or more sensor relays;
  one or more output devices; and
  one or more computer processors that:
  receive a signal from any of the one or more sensor relays, detecting the information related to the user;
  analyze the detected information;
  and either:
  send a signal to any of the one or more output devices, instructing the decision maker.

2. The system of claim 1 further comprising one or more movement devices.

3. A system as described in claim 2 wherein one or more of the movement devices is a moving walkway further comprising:
  a standing desk.

4. A system as described in claim 3 wherein said standing desk moves through any of the following means:
  a direct attachment to the user;
  a motor which moves the standing desk in response to user movement measured against one or more manufacturer defined or user defined set points as detected by any or any combination of sensor relays;
  any part of the moving platform moving;
  or any combination therein.

5. The system as described in claim 2 where one or more of the movement devices is an elliptical treadmill, circular treadmill, or layable connectible modular trackpad.

6. The system as described in claim 5 surrounded by one or more display apparatus comprising:
  one or more solar panels;
  a display panel overtop of said solar panels;
  wherein light may pass through said display panel, thereby supplying energy to said solar panels, which may in turn power said display panel.

7. The system as described in claim 6 wherein said solar panels may comprise a magnifying glass for amplifying the energy or heat collected.

8. The system as described in claim 6 further comprising one or more batteries for the storage of energy and/or one or more external solar panels.

9. A system as described in claim 1 further comprising one or more movement devices;
  wherein one or more movement device is a moving walkway;
  wherein said moving walkway spans the entire width of the area.

10. The system as described in claim 9, further comprising one or more platforms, separate from the moving walkway.

11. The system described in claim 10, further comprising:
  one or more motors;

one or more levers;

one or more pulleys;

or any combination therein;

wherein said motors, levers, pulleys, or any combination therein may be used to move said platform, such that an observer on said platform may move separately from the moving walkway.

12. The system described in claim 9 further containing a floor raised any level above the base of said moving walkway, said floor further comprising one or more holes;

such that a user standing in a hole will be on said moving walkway, whereas an observer not standing in a hole will be on said floor.

13. The system described in claim 2 wherein an observer can control one or more movement devices, one or more output devices, or any combination therein.

14. The area as described in claim 1 further comprising a plurality of sensor relays about the perimeter of the area, said sensor relays transmitting signals to and from any sensor relays monitoring the user, the user's output device, or one or more movement devices.

15. An apparatus comprising:

a movement device;

one or more sensor relays;

any number of output devices;

wherein the movement device and/or one or more output device may be adjusted based on transmissions between one or more of said sensor relays and one or more sensor relays monitoring the user.

16. The apparatus of claim 15 wherein the movement device is a circular or elliptical treadmill, wherein said circular treadmill further comprises a removable guide rails for users to enter and exit the apparatus or on which an output device can be mounted and move in a guided fashion, or which a physical guide system may be attached to for guiding the user around the treadmill.

17. The apparatus of claim 15 wherein the movement device is a rotating or spinning trackpad which utilizes a plurality of rollers, balls or any combination therein to move in direct response to the feedback received by the sensor relays from the user, such that the sphere allows the user to maintain their position despite increasing their velocity.

18. The apparatus of claim 17 further comprising one or more weight sensors within the movement device, to provide a feedback loop if a user enters, exits or leaps from the movement device.

19. The apparatus of claim 15 wherein one or more of said output devices is an augmented reality headset, virtual reality headset or mixed reality headset further comprising one or more sensors capable of transmitting information regarding detected motion to a computer network further comprising a database and network to transmit data regarding performance to a different augmented reality headset, virtual reality headset or mixed reality headset.

20. A method of teaching comprising the steps of:

having one or more students in motion through the use of one or more movement devices; presenting the student with educational material while the student is in motion;

said student assisted through the use of one or more sensor relays that may detect and relay signals, conveying information related to one or more sensor detected user performance related activities measured against one or more set points the user, controlling:

one or more output devices, one or more movement devices, or one or more computer processors;

at least one of said sensor relays being fitted to the user, and the control of the devices or processors being a response to whether the altering based on said sensor relay relayed information that is analyzed by a processor as being within any number of measured against one or more manufacturer predefined, observer defined, or user defined set-points.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention.

The invention is not intended to be limited to the preferred embodiments described above, but rather is intended to be limited only by the claims set out below. Thus, the invention encompasses all alternate embodiments that fall literally or equivalently within the scope of these claims.

Having thus described the invention, we claim:

1. A system comprising: one or more sensor relays; one or more output devices; and one or more computer processors that: receive a signal from any of the one or more sensor relays, detecting information related to one or more users; analyze the detected information; and either: send a signal to any of the one or more output devices, or send a signal to one or more movement devices, wherein the one or more movement devices receive one or more signals from the one or more computer processors or the one or more output devices, and the one or more movement devices adjusts velocity or resistance in response to the one or more signals received.

2. A system as described in claim 1 wherein one or more of the movement devices is a moving walkway further comprising:

a standing desk.

3. A system as described in claim 2 wherein said standing desk moves through any of the following means:

a direct attachment to the user;

a motor which moves the standing desk in response to user movement measured against one or more manufacturer defined or user defined set points as detected by any or any combination of sensor relays;

any part of the moving platform moving;

or any combination therein.

4. The system as described in claim 1 where one or more of the movement devices is an elliptical treadmill, circular treadmill, or layable connectible modular trackpad.

5. The system as described in claim 4 surrounded by one or more display apparatus comprising:

one or more solar panels;

a display panel overtop of said solar panels;

wherein light may pass through said display panel, thereby supplying energy to said solar panels, which may in turn power said display panel.

6. The system as described in claim 5 wherein said solar panels may comprise a magnifying glass for amplifying the energy or heat collected.

7. The system as described in claim 5 further comprising one or more batteries for the storage of energy and/or one or more external solar panels.

8. A system as described in claim 1
wherein the adjustment comprises comparing a current operational parameter value of the movement device to a target parameter value derived from the analysis of the detected information, calculating a difference between the current operational parameter value and the target parameter value, and incrementally modifying the velocity or resistance by predetermined adjustment increments when the calculated difference exceeds a threshold value.

9. The system as described in claim 1 wherein the adjustment occurs through a feedback control loop that samples the detected information at predetermined time intervals and applies velocity or resistance changes based on a rate of change calculation between successive samples.

10. The system described in claim 1 wherein the adjustment is implemented by accessing a stored user profile containing baseline performance metrics, comparing current detected information to the baseline metrics, and applying adjustment curves that scale the velocity or resistance changes based on the deviation from the baseline.

11. The system described in claim 1 wherein an observer can control one or more movement devices, one or more output devices, or any combination therein.

12. The system as described in claim 1 wherein the adjustment limits the rate of velocity or resistance change to predetermined maximum values when the detected information indicates user distress signals exceed safety thresholds.

\* \* \* \* \*